US009069700B2

(12) United States Patent
Ishiguro

(10) Patent No.: US 9,069,700 B2
(45) Date of Patent: Jun. 30, 2015

(54) STRUCTURAL MODEL OF G PROTEIN-COUPLED RECEPTOR AND METHOD FOR DESIGNING LIGAND CAPABLE OF BINDING TO G PROTEIN-COUPLED RECEPTOR USING THE STRUCTURAL MODEL

(71) Applicant: Suntory Holdings Limited, Osaka-Shi, Osaka (JP)

(72) Inventor: Masaji Ishiguro, Hyogo (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 0 days.

(21) Appl. No.: 13/692,859

(22) Filed: Dec. 3, 2012

(65) Prior Publication Data

US 2014/0025345 A1 Jan. 23, 2014

Related U.S. Application Data

(63) Continuation of application No. 10/473,681, filed as application No. PCT/JP02/03264 on Apr. 1, 2002, now abandoned.

(30) Foreign Application Priority Data

Mar. 30, 2001 (JP) ................................. 2001-101510

(51) Int. Cl.
*G06F 19/12* (2011.01)
*G01N 33/566* (2006.01)
*G06F 19/16* (2011.01)
*C07K 14/72* (2006.01)
*G01N 33/68* (2006.01)

(52) U.S. Cl.
CPC .............. *G06F 19/12* (2013.01); *C07K 14/723* (2013.01); *C07K 2299/00* (2013.01); *G01N 33/566* (2013.01); *G01N 33/6803* (2013.01); *G06F 19/16* (2013.01)

(58) Field of Classification Search
CPC ......... G06F 19/10; G06F 19/12; G06F 19/16; G06F 19/18; G06F 19/26; G06F 19/701; G06F 19/703; G06F 19/704; G06F 19/708; C07K 2999/00; C07K 14/723; C40B 50/02; G01N 33/566; G01N 33/6803
See application file for complete search history.

(56) References Cited

FOREIGN PATENT DOCUMENTS

| JP | 06-309385 A | 11/1994 |
|---|---|---|
| JP | 07-133233 A | 5/1995 |
| JP | 2000-023676 | 1/2000 |
| JP | 2000-023677 | 1/2000 |
| JP | 2000-050875 | 2/2000 |
| JP | 2000-152792 | 6/2000 |
| JP | 2000-166576 | 6/2000 |
| JP | 2000-175690 | 6/2000 |
| JP | 2000-175691 | 6/2000 |
| JP | 2000-295995 | 10/2000 |
| JP | 2000-354500 | 12/2000 |
| JP | 2001-029083 A | 2/2001 |
| JP | 2001-029084 A | 2/2001 |
| JP | 2001-054388 A | 2/2001 |
| JP | 2001-054389 A | 2/2001 |

OTHER PUBLICATIONS

M. Ishiguro, "Modeling of G Protein-Coupled Receptors for Drug Design," Chapter 12: In G Protein-Coupled Receptors: Structure, Function, and Ligand Screening, T. Haga et al., eds., CRC Taylor & Francis, 2006, pp. 283-302.
K. Palczeski et al., "Crystal Structure of Rhodopsin: A G Protein-Coupled Receptor", Science, vol. 289, Aug. 4, 2000, pp. 739-745.
Yoshiki Miyake, "Receptor G Tanpakushitsu Ketsugo Jotai no Kozo Simulation", Kenkyu Seika Hokokusho, Mar. 1999, pp. 95-98.
Spring-8 Information, vol. 5, No. 6, (2000), pp. 394-400.
Journal of The American Chemical Society, vol. 122, No. 3, (2000), pp. 444-451.
Kagaku to Kogyo, vol. 44, No. 5, (1991), pp. 780-785.
Kagaku, vol. 66, No. 8, (1996), pp. 556, 561-566.
Yuki Gosei Kagaku Kyokaishi, Vo. 54, No. 5, (1996), pp. 427-436.
J. Mass Spectrom. Soc. Jpn., vol. 47, No. 3, (1999), pp. 135-139.
Fharmacia vol. 37. No. 4, Apr. 1, 2001. pp. 291-360.
Farrens et al., "Requirement of Rigid-Body Motion of Transmembrane Helices for Light Activation of Rhodopsin," Science, 1996, vol. 274, pp. 768-770, American Association for the Advancement of Science, Washington, D.C., USA.
Ballesteros et al., "G protein-coupled receptor drug discovery: Implications from the crystal structure of rhodopsin," Current Opinion in Drug Discovery & Development, 2001, vol. 4, No. 2, PharmaPress Ltd., London, England.
Hargrave, "Future directions for rhodopsin structure and function studies," Behavioral and Brain Sciences, 1995, vol. 18, No. 3, Cambridge University Press, Cambridge, MA, USA.

(Continued)

*Primary Examiner* — Lori A Clow
(74) *Attorney, Agent, or Firm* — Drinker Biddle & Reath LLP

(57) ABSTRACT

The present invention provides a method for constructing a three-dimensional structural model of an activated intermediate of a G protein-coupled protein receptor (GPCR) or a complex between a GPCR and a ligand. The three-dimensional structural model may be used to identify, screen, search, evaluate, or design GPCR agonists or antagonists. In a representative embodiment, a three-dimensional structural model of a photoactivated intermediate of rhodopsin is constructed using molecule modeling software and structural coordinates of the crystal structure of rhodopsin. The three-dimensional structural model of rhodopsin is subsequently used to construct structural models of activated intermediates of other GPCRs.

9 Claims, 17 Drawing Sheets

(10 of 17 Drawing Sheet(s) Filed in Color)

(56) References Cited

OTHER PUBLICATIONS

Insight II User's Manual (release Mar. 2000); Contents pp. 1-18 and Chapter 2, pp. 1-44.

EP 02 708 749 A to Suntory Holdings Ltd., Supplemental submission to the EPO in advance of oral proceedings, including 8 exhibits, filed Mar. 17, 2014.

EP 02 708 749 A to Suntory Holdings Ltd., Submission of Suzuki reference, filed Mar. 5, 2014.

Suzuki et al., "Identification of G protein-coupled receptor 120-selective agonists derived from PPARγ agonists," *J. Med. Chem.* 51: 7640-44 (2008).

Akuzawa et al., "Structural modelling and mutation analysis of a nociception receptor and its ligand complexes," *J. Biochem.* 141: 907-16 (2007).

Hossain et al., "Mechanism of inverse agonist action of sarpogrelate at the constitutively active mutant of human 5-HT$_{2A}$ receptor revealed by molecular modeling," *Biol. Pharm. Bull.* 35: 1553-59 (2012).

Ishiguro, "Conformational analysis of Glu181 and Ser186 in the metarhodopsin I state," *ChemBioChem* 5: 1204-09 (2004).

Ishiguro, "Ligand-binding modes in cationic biogenic amine receptors," *ChemBioChem* 5: 1210-19 (2004).

Ishiguro, "Modelling of photointermediates suggests a mechanism of the flip of the β-ionone moiety of the retinylidene chromophore in the rhodopsin photocascade," *ChemBioChem* No. 2-3: 228-231 (2003).

Ishiguro, "Structural models of the photointermediates in the rhodopsin photocascade, lumirhodopsin, metarhodopsin I, and metarhodopsin II," *ChemBioChem* 5: 298-310 (2004).

Sun et al., "Structure-activity relationships of GPR120 agonists based on a docking simulation," *Mol. Pharmacol.* 78: 804-810 (2010).

EP 02 708 749 A to Suntory Holdings Ltd., Response to summons to attend oral hearings, filed Mar. 3, 2014, including Main Request and Auxiliary Requests.

EP 02 708 749 A to Suntory Holdings Ltd., Official Action submitted by the EPO Aug. 29, 2013.

EP 02 708 749 A to Suntory Holdings Ltd., Response, including 2 exhibits, to Official Action dated Jun. 23, 2009, filed Jan. 4, 2010.

EP 02 708 749 A to Suntory Holdings Ltd., Official Action dated Jun. 23, 2009.

EP 02 708 749 A to Suntory Holdings Ltd., Response to Official Action dated Jun. 12, 2007, filed Dec. 24, 2007.

FIGURE 1B

TM 1
                            41
1: PEVVFIVLVA ASLSLVTIIG NLLVMVSIKV N
                       36
2: ACKITITVVL AVLILITVAG NVVVCLAVGL N
                       52
3: QBKNWSALLT AVVIIITIAA NLLVIMAVSL E
                       52
4: PHYNYYATLL TLLHAVIVFG NVLVCMAVSR E
                       51
5: VMVVGMGIVM SLIVLAIVFG NVLVITAIAK P
                       55
6: WQFSMLAATM FLLIMLGFFI NFLTLYVTVQ H

TM 4
            148
1: RTTKMAGWMI AAAWVLSPIL WAPAIL
       143
2: VTPVRVAISL VLIWVLSITL SFLSTH
       200
3: NSRTKAFLKI LAVWTLSVGI SMPIPV
       159
4: SSKRRVTVMI SIVWVLSFTI SCPLLF
       158
5: LTKNKARVII LMVWIVSGLT SFLPIQ
       161
6: FGENHAIMGV AFTWVMALAC AAPFLV

TM 7
    426
1: GYWLCYINST LNPACYALCN
       278
2: VLWLGYANSA LNPILYAALN
       370
3: FVWIGYLSSA VNPLVYTLFN
       416
4: PTWLGYVNSA VNPIIYTTFN
       316
5: IRWIGYVNSG FNPLIYCRSP
       296
6: PAFFAKTSAV YNPVIYIMMN

TM 2
                            69
1: VNNYFLPSLA CADLIIGVFS MNLYTLYTVI
                       64
2: LTNCFIVSLA ITDLLLGLLIV LPFSAIYQLS
                       120
3: ATNYFLMSLA IADMLLGFLIV MPVSMLTLIY
                       80
4: TTNYLIVSLA VADLLVATLIV MPWVVYLEVV
                       79
5: VTNYFITSLA CADLVMGLAV VPFGAAHILM
                       99
6: PLNYILLNLA VADLFMVFGG PTTTLYTSLH

TM 5
            190
1: AAVTFGTAIA AFYLPVTIMT VLYWHI
       186
2: EVYGLVDGLV TFYLPLHIMC ITYYRI
       239
3: DNFVLIGSFV SFFIPLRIMV ITYPLT
       193
4: PAFVVYSSIV SFYYPFIVTL LVYIKI
       203
5: QAVAIASSIV SFYYPLVIMV FVYSRV
       211
6: BSIFVIYMFVV HFIIFLIVIF FCYGQL

TM 3
                           103
1: GPVVCDLWLA LDYVVSNASV MNLLIISFDR YFCVT
                      98
2: GKVFCNIYTS LRVMLCTASI LNLFMISLDR YCAVM
                      155
3: PSKLCAVWIY LEVLFSTASI MHLCAISLDR YVAIQ
                      114
4: SRIHCDIFVT LRVMMCTASI LNLCAISIDR YTAVA
                      113
5: GNFWCEFWTS IDVLCVTASI ETLCVIAVDR YFAIT
                                   135
6: GFTGCNLEGF FATLGGETAL WSLVVLAIER YVVVC

TM 6
            400
1: FPSREKKVTR TILAILLAFI ITWAPYNVMV LINTFC
       247
2: ATIREHKATV TLAAVMGAFI ICWFPYFTAF VYRGLR
                                336   343
3: SISNEQKACK VLGIVFFLFV VMWCPFFITN IMAVIC
                                365   393
4: SQQKEKKATQ MLAIVLGVFI ICWLPFFITH ILNIHC
                                286   293
5: FCLKEHKALK TLGLIMGTFT LCWLPFFIVN FVHVIQ
                                   265
6: TQKAEKEVTR MVIIMVIAFL ICWLPYAGVA FYIFTH

STRUCTURAL MODEL OF G PROTEIN-COUPLED RECEPTOR AND METHOD FOR DESIGNING LIGAND CAPABLE OF BINDING TO G PROTEIN-COUPLED RECEPTOR USING THE STRUCTURAL MODEL

This is a continuation of co-pending application Ser. No. 10/473,681, filed Feb. 17, 2004, which is a National Stage of International Application No. PCT/JP02/03264, filed Apr. 1, 2002, which claims the benefit of priority under 35 U.S.C. §119(a) to JP 2001-101510, filed Mar. 30, 2001, the entire contents of each of which are incorporated by reference herein in their entirety.

TECHNICAL FIELD

The present invention relates to a structural model for receptor/ligand complexes of G protein-coupled receptors (which may be referred to simply as 'GPCRs,' hereinafter) and ligands capable of binding to G protein-coupled receptors. It also relates to a method for creating a three-dimensional structural model for activated intermediates of G protein-coupled receptors in the structural model for the receptor/ligand complexes, as well as to structural models of the complexes or the activated intermediates of G protein-coupled receptors obtained by this method. The present invention further relates to a three-dimensional coordinate for determining these structural models.

The present invention further relates to a method for using the three-dimensional structural model of G protein-coupled receptors or a method for using the three-dimensional coordinates for determining the structural model in identifying, screening for, searching for, evaluating, and designing ligands that act as an agonist (full agonist or partial agonist) or an antagonist (antagonist or inverse antagonist) upon binding to G protein-coupled receptors.

The present invention further relates to a method for using the three-dimensional structural model of the G protein-coupled receptors or a method for using the three-dimensional coordinate for determining the structural model in designing mutants of G protein-coupled receptors (e.g., constitutively active mutants) or in screening for and searching for orphan receptors and identifying their ligands in vivo.

BACKGROUND ART

Transmission of extracellular information into the cell in most cases requires mediation by membrane proteins that have transmembrane domains. G protein-coupled receptors (GPCRs) are signal-transmitting membrane proteins that have seven transmembrane domains and make up a receptor family that can bind various physiological peptide ligands, including biological amines such as dopamine and serotonin, lipid derivatives such as prostaglandin, nucleic acids such as adenosine, amino acids such as GABA, angiotensin II, bradykinin, and cholecystokinin. Serving also as receptors for extracellular transmitters responsible for the senses of vision, taste and smell, GPCRs are important membrane proteins that play a key role in signal transduction.

The recent progress in completing the human genome sequence is expected to lead to discovery of many orphan receptors that are suspected of being GPCR. If successfully identified, the ligands for these GPCRs will allow for more effective development of pharmaceutical products. Thus, devising a structural model for G protein-coupled receptor/ligand complexes and devising a three-dimensional structural model for G protein-coupled receptors in the structural model of the complexes will provide an important approach to the future development of pharmaceutical products, as will the identification, screening, searching, evaluation, and designing methods of ligands that take advantage of these structural models.

In fact, a number of patent applications entitled "novel G protein-coupled receptor protein and its DNA" have recently been filed, including Japanese Laid-Open Patent Publications No. 2001-29083, No. 2001-29084, No. 2001-54388, No. 2001-54389, No. 2000-23676, No. 2000-23677, No. 2000-50875, No. 2000-152792, No. 2000-166576, No. 2000-175690, No. 2000-175691, and No. 2000-295995, to name a few. Some applications, such as Japanese Patent Laid-Open Publication No. 2000-354500, disclose methods for screening for ligands that bind to G protein-coupled receptors while other applications concern methods for cloning expression of G protein-coupled receptors.

Ligands that bind to a particular GPCR are generally classified into agonists and antagonists. According to the latest pharmacological classification standards, the former is further divided into full agonists and partial agonists and the latter into inverse agonists and antagonists.

These ligands are classified not by their affinity for the receptor, but by the degree to which the ligand activates the receptor. For example, assuming the activity elicited by binding of a full agonist to be 100%, a partial agonist elicits a 50 to 70% activity.

In comparison, binding of an antagonist suppresses the activity to 5 to 10% of what is elicited by the binding of a full agonist, and binding of an inverse agonist completely eliminates the activity (0% activity).

Even when unbound to ligands, many GPCRs exhibit 5 to 10% of the activity expected by the binding of a full agonist. Thus, it is believed that antagonists bind to physiologically inactive receptor conformations. This suggests that binding of other types of ligands brings about conformational change of GPCR. Thus, the binding of ligands and subsequent conformational change of receptors are believed to play an important role in information transmission mediated by GPCR.

G protein-coupled receptors (GPCR), which share seven transmembrane domains, are classified into different families based on the homology of their amino acid sequences. In one such GPCR family, each member has high homology to rhodopsin, a photoreceptor membrane protein. The GPCRs of this family share highly conserved amino acid residues in their transmembrane domains. These amino acid residues are believed to play an important role in the functioning of GPCRs.

Structural and functional studies of GPCR have been conducted by analyzing three-dimensional structure of rhodopsin through two-dimensional cryoelectron diffraction crystallography and X-ray crystallography (Palczewski, K. et al., *Science* 289, 739-745. (2000)). Also, structures of the receptor proteins and the chromophores to serve as ligands, as well as the receptors' conformational changes, have been studied using FT-IR and Raman spectroscopy (Sakmar, T. P., *Prog. Nucleic Acid Res.* 59, 1-34 (1998)).

Based on the results of two-dimensional, low-resolution, cryoelectron diffraction crystallography, a three-dimensional structural model of rhodopsin was first constructed. More recently, more detailed three-dimensional structure of rhodopsin was revealed by X-ray crystallography. This structure was consistent with the structural characteristics previously expected from the results of FT-IR and Raman spectroscopy and made it possible to formulate assumptions about the roles of some parts of the highly conserved amino acid residues of GPCRs.

For example, of the highly conserved amino acid residues of rhodopsin, the Glu134-Arg135-Tyr136 triplet (ERY triplet, which corresponds to Asp-Arg-Tyr, or DRY triplet, in other GPCRs) of the third transmembrane helix (TM3) (hereinafter, each of the seven transmembrane helices may be denoted by abbreviation followed by respective consecutive numbers: n th helix is denoted as TMn (e.g., TM3)) located on the inside of the cell plays a significant role in the activation of G protein. It has been shown that the protonation of ionized Glu134 in metarhodopsin II (described later), an activated conformation of rhodopsin, triggers activation of G-protein (Arnis, S. & Hofmann, K. P., *Proc. Natl. Acad. Sci. USA*, 90, 7849-7853, 1993). Also, a significant involvement of Glu and Arg in the activation of GPCRs is suggested.

On the other hand, it is suggested that a highly conserved Pro residue found in TM6 and TM7 (Pro 267 in TM6) is responsible for the kink structure characteristic of these two helices. However, the role of the kink in the functioning of GPCRs still remains unclear.

Hydrophilic amino acid residues Asn55, Asp83, Asn302 found in TM1, TM2, and TM7, respectively, are linked to one another via hydrogen bonds. Also, Tyr306 residue conserved among TM7s is linked, through hydrophobic interaction, to a residue of C-terminal helix located on the inside of the cell. These interactions are believed to contribute to stabilizing the structure.

Rhodopsin is also one of the GPCRs closely studied for its conformational change and functions. Rhodopsin consists of 11-cis-retinal, a chromophore, and opsin, a protein component with the seven transmembrane domains. 11-cis-retinal is covalently bonded to Lys296 to form a Schiff base. This Schiff base is protonated and is thus responsible for the shift of the maximum UV absorbance ($\lambda$max) of the chromophore to a long-wavelength range of 498 nm.

When illuminated, rhodopsin is converted to highly unstable bathorhodopsin (which may be referred to simply as 'Batho,' hereinafter), which has the UV absorbance shifted to an even longer wavelength range. Upon this, 11-cis-retinal is converted to 11-trans-retinal, an all-trans chromophore. The unstable, high-energy Batho is then sequentially converted to different intermediates in the order of lumirhodopsin ('Lumi,' hereinafter), metarhodopsin I ('Meta I,' hereinafter), metarhodopsin Ib ('Meta Ib,' hereinafter), and metarhodopsin II ('Meta II,' hereinafter) as the chromophore and opsin thermally undergo conformational changes (Tachibanaki, S. et al., *Biochemistry* 36, 14173-14180 (1997)) (the photoreaction process is shown in FIG. 1).

Under physiological conditions, Lumi is converted to Meta II via an intermediate known as metarhodopsin $I_{380}$ ('Meta $I_{380}$,' hereinafter) (Thorgeirsson, T. E. et al., *Biochemistry* 32, 13861-13872 (1993)) (FIG. 1).

Because the activation of G protein (transducin) takes place at Meta II stage, 11-cis-retinal attached to rhodopsin is regarded as an inverse agonist while all-trans retinal attached to Meta II can be regarded as a full agonist. Since the same chromophore of rhodopsin changes from an inverse agonist to a full agonist upon illumination of light, its conformational changes can be studied by observing changes in absorption spectrum.

The conversion of rhodopsin to Batho is a rapid process that takes place within 200 fs. Each conformational change leading to Meta II takes about a few milliseconds, which is long enough to allow a protein to undergo a significant conformational change involving spatial displacement of the secondary structures of the protein. It has been shown that the conformational change of opsin causes the beta-ionon moiety of the retinal chromophore to change its direction from the 6th helix (TM6) to the 4th helix (TM4) (Bohan, B. et al., *Science*, 288, 2209-2212 (2000)). This implies that the arrangement of helices has been altered as a result of photoisomerization.

Also, Khorana and Hubbell in their experiment illuminated light onto a mutant rhodopsin, which has been spin-labeled in a site-directed manner by taking advantage of SH groups in the mutant site-specifically substituted with cysteine, and demonstrated that the conformational changes of rhodopsin to Meta II are accompanied by conformational changes of the intracellular loops and helices. They proposed a model in which the entire TM6 helix undergoes significant rotation. The model implies considerable conformational changes of membrane proteins (Farrens, D. L. et al., *Science* 274, 768-770 (1996)).

Light energy absorbed by the chromophore is harnessed to cause initial conformational change of opsin. Transition to the final active form, the Meta II conformation, begins with proton transfer from the protonated Schiff base to its counterion, Glu 134 in TM3, to form neutral Schiff base. The neutralization of the Schiff base allows movement of the helix and, ultimately, the rotation of TM6, causing the shift to the Meta II conformation.

Of the different photoactivated intermediates of rhodopsin, the final Meta II conformation has proven to be the only form that has been fully activated (Khorana, H. G. *J. Biol. Chem.*, 267, 1-4 (1992)). However, opsin without the chromophore is known to exhibit approximately 5% activity, and mutant opsin in which Glu134, which serves as a counterion of the protonated Schiff base, has been substituted with Gln exhibits approximately 50% activity even in the absence of the chromophore.

This mutant opsin is known to be deactivated when 11-cis-retinal is added and irradiation with light converts it to all-trans-retinal, which in turn is converted to fully activated Meta II conformation. Thus, it has been shown that opsin has several active forms (Kim, J.-M. et al., *Proc. Natl. Acad. Sci. USA*, 94, 14273-14278 (1997)).

It is also known that G-protein (transducin) does not bind opsin when rhodopsin is in its Meta I state while it binds opsin without activating it when rhodopsin is in its Meta Ib state (Tachibanaki, S. et al., *Biochemistry* 36, 14173-14180 (1997)).

As described, a series of events, including conformational changes of opsin and its interaction with G-protein, and subsequent activation of G-protein, take place over the course of the process from Lumi to Meta II. During this process, the rotation of TM6, essential for the activation of rhodopsin, provides the G protein-coupled receptor with the structural specificity required for ligand recognition. Specifically, it has been shown that the amino acid residues in the ligand binding site involved with TM6 before the rotation of TM6 are different than the ones involved with TM6 after the rotation of TM6, and amino acid residues that serve to recognize full agonists are different than those that serve to recognize antagonists.

In fact, mutants are often found in which alteration of some of the amino acid residues in TM6 affects the binding of full agonists but not the binding of antagonists. Such phenomenon will be explained by taking into account the conformational changes of the receptors.

Studies on conformational changes of rhodopsin suggested that the arrangement of TMs is significantly different between the receptors that bind antagonists and the receptors that bind agonists. For this reason, the crystal structure of rhodopsin does not solely provide a structural model for every receptor/ligand complex.

A comparison between the crystal structure of rhodopsin and a structural model for Meta II in accordance with the present invention is shown in FIG. 2. The significant displacement of highly conserved Trp265 in TM6 suggests that different amino acid residues are involved in recognizing agonists and antagonists.

As described above, several experiments demonstrated that photoactivation of rhodopsin brings about conformational changes of opsin (See, for example, Farrens, D. L. et al., *Science* 274, 768-770 (1996). Kim, J.-M. et al., *Proc. Natl. Acad. Sci. USA*, 94, 14273-14278, (1997)). Nonetheless, the nature of specific conformational change has yet to be understood.

Accordingly, it is an objective of the present invention to simulate three-dimensional structures of these photoactivated intermediates of rhodopsin by means of computer graphics and scientific calculation and to thereby construct structural models for their complexes formed with ligands (chromophores) that can bind rhodopsin as well as three-dimensional structural models for the activated rhodopsin intermediates in the structural models of the complexes.

It is another objective of the present invention to provide a method for identifying, screening for, searching for, or evaluating whether a given ligand is a full agonist, a partial agonist, an antagonist, or an inverse agonist by constructing three-dimensional models for general G protein-coupled receptors (GPCRs) other than rhodopsin from the three-dimensional structural models for the activated intermediates of rhodopsin and, for each of the three-dimensional models, constructing structural models for their complexes formed with ligands and analyzing the interaction of GPCRs with corresponding ligands. It is still another objective of the present invention to provide a method for designing a novel ligand molecule that acts as an agonist or an antagonist of a GPCR.

DISCLOSURE OF THE INVENTION

In an effort to achieve the aforementioned objectives, the present inventor has succeeded in constructing structural models consistent with available experimental data for each of the known photoactivated intermediates of rhodopsin: Lumi, Meta I, Meta Ib, Meta $I_{380}$ and Meta II.

Specifically, the present inventor has directed his attention to amino acid residues highly conserved among GPCRs that show high homology to rhodopsin and has succeeded in revealing their role by generating and then optimizing the structural models for rhodopsin intermediates by means of a molecule modeling software Insight II-Discover 3 (Molecular Simulations Inc., USA) using the three-dimensional structural coordinates for the crystal structure of rhodopsin (Palczewski et al., *Science*, 289, 144-167 (2000)). In this manner, the present inventor has successfully simulated the conformational changes of rhodopsin and analyzed its interaction with ligands.

The conformational change of rhodopsin takes place in the following manner: TM3 of the seven transmembrane helices (TM1-7), which strongly interacts with TM7, is first mobilized, and the disulfide bond that Cys110, a highly conserved residue on the extracellular side of TM3, forms with Cys187 causes the helix on the cytoplasmic side to swivel about Cys110 in a pendulum-like fashion toward the extracellular side. This in turn causes the movement of adjacent TM4.

On the other hand, TM1, TM2, and TM7 are not subjected to conformational changes because of hydrogen bonds between the highly conserved amino acid residues and form a cluster of helices less susceptible to the movement of TM3.

TM3 and TM4 move in such a manner that the ligand-binding site is enlarged. This movement is controlled by the interaction between Glu134-Arg135-Tyr136, a highly conserved sequence on the cytoplasmic side of TM3, and Glu247 on the cytoplasmic side of TM6. The movement of TM3 and TM4 lasts until the Meta $I_{380}$ stage, during which time structures corresponding to Lumi, Meta I, and Meta Ib are formed.

The structure of Meta II is generated from Meta $I_{380}$ or similar structures: TM6, as viewed from the cytoplasmic side, rotates clockwise by 100° and then translate to come close to TM3. Upon this, the conformational change in TM6 causes TM5 to move to where it is free from structural interference. Finally, TM4 moves toward TM5 to form the structure of Meta II.

As described, the seven transmembrane helices (TMs) of rhodopsin are divided into three domains depending on the role that they play in the conformational change: a first domain including TM1, TM2, and TM7, a second domain including TM3 and TM4, and a third domain including TM5 and TM6. By investigating contribution of each of the three domains to the conformational change of rhodopsin, it has been made possible to generate structures of all of the intermediates between rhodopsin and Meta II.

Accordingly, the present invention provides a three-dimensional structural model or a three-dimensional coordinate for determining the structural model used for identifying, searching for, screening for, evaluating, or designing a ligand that can bind a G protein-coupled receptor to act as an agonist or an antagonist.

Specifically, the present invention provides a three-dimensional structural model or a three-dimensional coordinate for determining the structural model, in which the activated intermediate of the G protein-coupled receptor is an intermediate of activated rhodopsin.

More specifically, the present invention provides a three-dimensional structural model or a three-dimensional coordinate for determining the structural model, in which the structural model of the activated rhodopsin intermediate is a metarhodopsin II structural model, a metarhodopsin I structural model, a metarhodopsin Ib structural model, or a metarhodopsin $I_{380}$ structural model.

The present invention further provides a method for constructing three-dimensional structural models of activated intermediates of G protein-coupled receptors other than rhodopsin by means of the structural model of the four activated rhodopsin intermediates.

More specifically, the present invention provides a method for constructing a structural model, the method comprising the steps of introducing amino acid substitution and insertion or deletion of amino acid residues on the loop regions by means of the structural model of the four activated rhodopsin intermediates based on the homology between the amino acid sequence of rhodopsin and the amino acid sequence of different G protein-coupled receptor; and subsequently optimizing the structure by using a molecule modeling software to construct a structural model.

The present invention further provides a computer storage medium that stores all or part of the above-described coordinate of the three-dimensional model for use in identifying, screening for, searching for, evaluating, or designing a ligand that binds the G protein-coupled receptor to act as an agonist or an antagonist.

The present invention further provides a method for identifying, screening for, searching for, evaluating, or designing a ligand that binds a G protein-coupled receptor to act as an agonist, the method comprises the step of using the above-described three-dimensional structural model, the three-dimensional coordinate for determining the structural model, or the computer storage medium storing the coordinate.

In particular, the present invention provides a method for identifying, screening for, searching for, evaluating, or designing the agonist, characterized in that, of the three-dimensional structural models or the three-dimensional coordinates for determining the structural models, the metarhodopsin II (Meta II) or the metarhodopsin $I_{380}$ (Meta $I_{380}$) structural model or the three-dimensional coordinate for determining the structural model, or the structural model constructed based on the metarhodopsin II (Meta II) or the metarhodopsin $I_{380}$ (Meta $I_{380}$) structural model or the three-dimensional coordinate for determining the structural model is used.

The present invention also provides a method for identifying, screening for, searching for, evaluating, or designing a ligand capable of binding a G protein-coupled protein to act as an antagonist, the method comprising the step of using the above-described three-dimensional structural model or the three-dimensional coordinate for determining the structural model, or the computer storage medium storing the coordinate.

In particular, the present invention provides a method for identifying, screening for, searching for, evaluating, or designing the antagonist, characterized in that, of the above-described three-dimensional structural models or the three-dimensional coordinates for determining the structural models, the metarhodopsin Ib (Meta Ib) or the metarhodopsin I (Meta I) structural model or the three-dimensional coordinate for determining the structural model or the structural model constructed based on the metarhodopsin Ib (Meta Ib) or the metarhodopsin I (Meta I) structural model or the three-dimensional coordinate for determining the structural model is used.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 18 is a diagram showing a homology in amino acid sequences of the seven transmembrane domains among rhodopsin and other GPCRs. (SEQ ID NOS: 1-42 are disclosed in the Sequence Listing respectively in order of appearance.)

DETAILED DESCRIPTION

Figure 1:
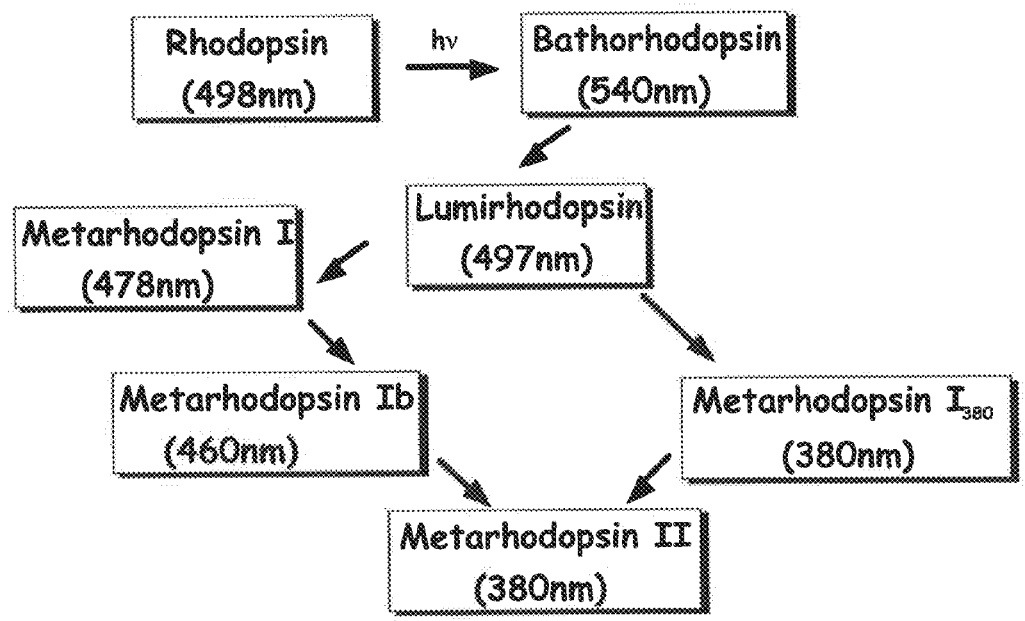
FIG. 1 is a diagram showing the photoreaction process of rhodopsin.
Figure 2:
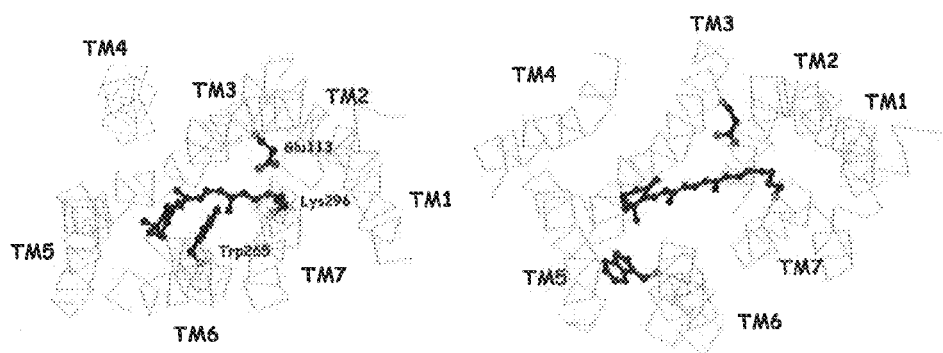
FIG. 2 is a diagram showing a comparison between crystal structural model of rhodopsin and a structural model of Meta II in accordance with the present invention.
Figure 3:
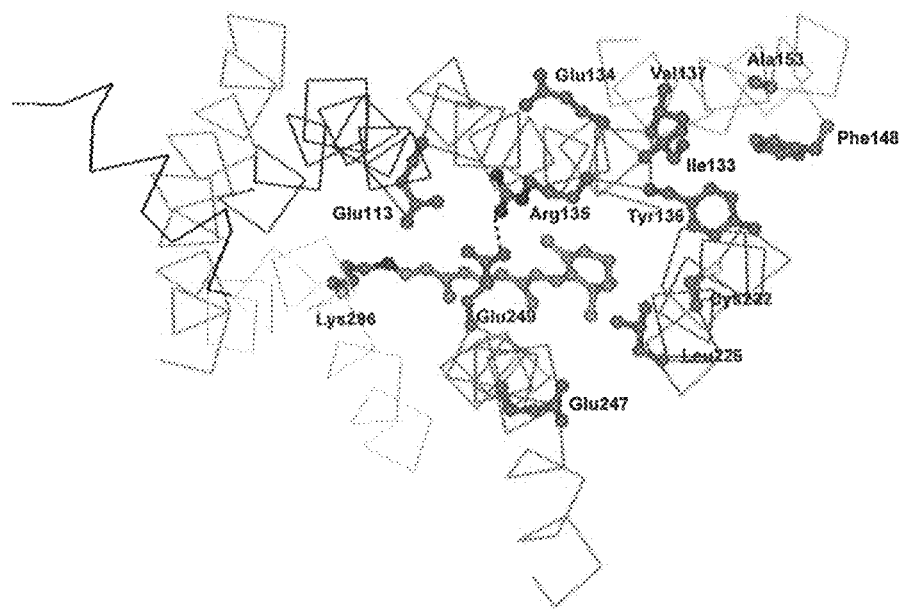
FIG. 3 is a structural model for a Meta II-ligand (chromophore) complex in accordance with the present invention.
Figure 4:
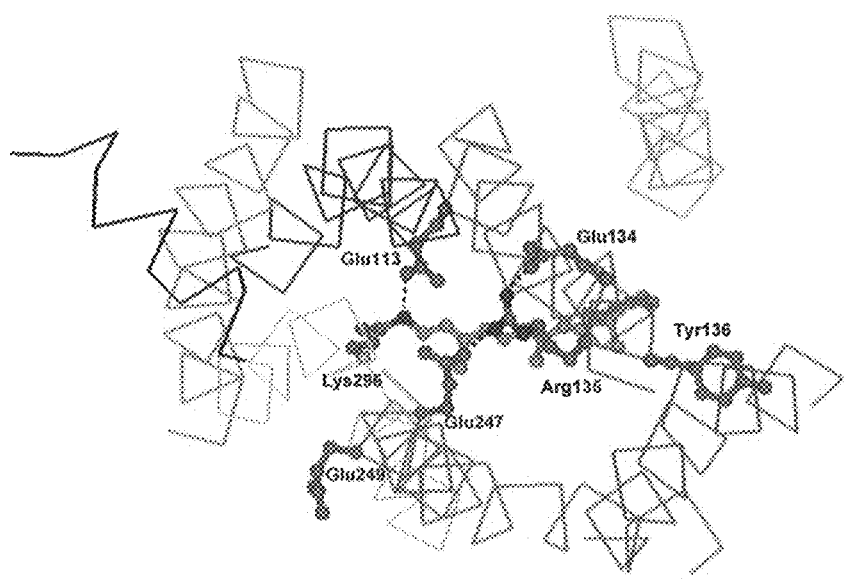
FIG. 4 is a structural model for a Meta I-ligand (chromophore) complex in accordance with the present invention.
Figure 5:
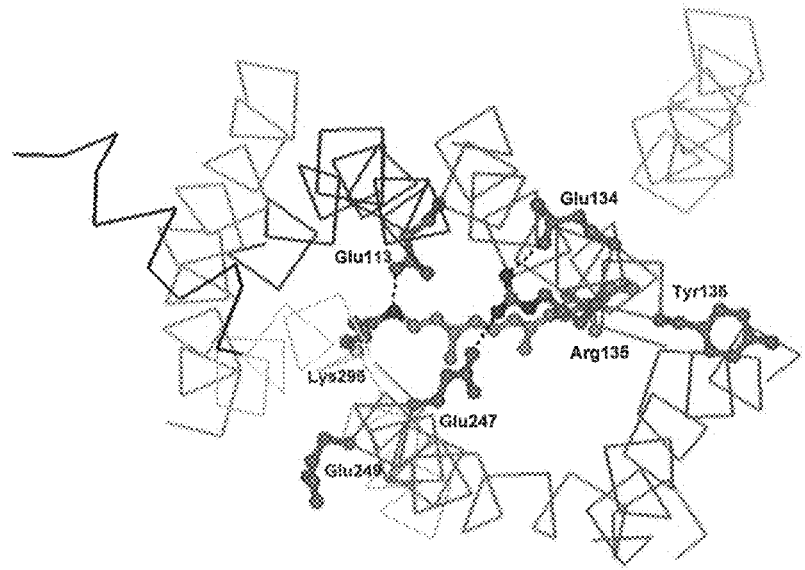
FIG. 5 is a structural model for a Meta Ib-ligand (chromophore) complex in accordance with the present invention.
Figure 6:
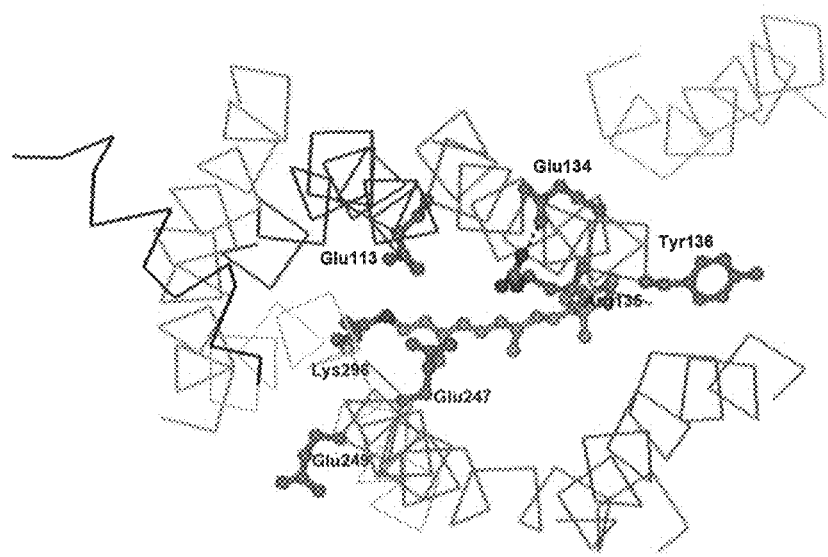
FIG. 6 is a structural model for a Meta $I_{380}$-ligand (chromophore) complex in accordance with the present invention.

In this specification, amino acids are represented by three-letter codes or single-letter codes as defined by IUPAC and IUB.

By "identifying a ligand," it is meant to determine whether a certain compound is an agonist (a full agonist or a partial agonist), an antagonist (an antagonist or an inverse antagonist), or neither of these.

By "screening or searching for a ligand," it is meant to find compounds having activity as an agonist or an antagonist in a set of naturally occurring or synthetic compounds.

Although some may agree that the term "screening" refers to selecting desired compounds from an available set or a library of compounds whereas the term "searching" refers to finding new compounds existing in nature, these terms are used interchangeably in this specification.

As used herein, the term "evaluation" has substantially the same meaning as "identification." Nonetheless, the term is preferentially used when a certain compound is discussed in terms of the magnitude of its activity as an agonist or an antagonist.

As used herein, the phrase "a structural model based on the structural models of activated rhodopsin intermediates" is meant to encompass not only the structural models for the activated intermediates of G protein-coupled receptors (GPCRs) other than rhodopsin that are constructed based on the above-described structural model of rhodopsin, but also the structural models for the mutants of the G protein-coupled receptors and the activated intermediates of the mutants.

Using three-dimensional coordinates with a molecule modeling software Insight II-Discover 3 (Molecular Simulations Inc., USA) that can determine the crystal structure of rhodopsin by means of X-ray diffraction crystallography (Palczewski et al., Science, 289, 144-167 (2000)), a structural model was generated for each of the intermediates and each structure was optimized.

Specifically, this is done as follows: TM3 is swung about the Cα carbon of Cys110 to serve as the pivot point while the distance to TM2 is kept at 5 Å or more. The magnitude of the swing is determined by taking into consideration the interaction of TM6 with Glu247 for each of Lumi, Meta I, Meta II, Meta Ib, and Meta $I_{380}$ structures. Specifically, in each of Lumi, Meta I, Meta Ib, and Meta $I_{380}$, Cys140 on TM3 is swung in such a manner that Cys140 is spaced from TM6 by a distance of 1.6 Å, 4.3 Å, 6.8 Å, and 9.0 Å, respectively. Furthermore, N-terminal (Glu150) of the portion of TM4 that would interfere with TM3 is swung toward TM5 about Gly174 on the C-terminal of the helix to serve as the pivot point by a distance of 3.5 Å, 7.4 Å, 12.1 Å, and 17.1 Å, respectively, to avoid interference. The structures so generated are optimized at 300 K by means of molecular kinetics and molecular dynamics so that Cα carbons of the amino acids can be fixed as firmly as possible.

As for the structure of Meta II, TM6 is rotated clockwise by an angle of 100 degrees as viewed from the intracellular side, and the distance between the residues on TM6 and the residues on TM3 is monitored and is decreased to a minimal distance that does not cause steric interference. Upon this, TM5 is twisted about Asn200 in a direction that can avoid steric interference resulting from the rotation of TM6. TM4 is then translated by a distance of 4.1 Å to place it between TM3 and TM5.

As a result, the distance between the Cα-carbon of Cys140 on TM3 and the Cα-carbon of Ala246 on TM6 becomes 12.7 Å and the Cα-carbon of Cys140 on TM3 is positioned at 4.8 Å from Glu150 on TM4. Leu226 on TM5 is positioned at a distance of 10.5 Å from Ala246 on TM6. TM5 and TM4 are moved so that they do not sterically interfere with TM6. The structures so generated are optimized at 300 K by means of molecular kinetics and molecular dynamics so that Cα carbons of the amino acids can be fixed as firmly as possible.

As described, the seven transmembrane helices of rhodopsin are divided into three domains depending on the role that they play in the conformational change of rhodopsin: a first domain including TM1, TM2 and TM7, a second domain including TM3 and TM4, and a third domain including TM5 and TM6. By investigating contribution of each of the three domains to the conformational change of rhodopsin, it has been made possible to generate structures of all of the intermediates between rhodopsin and Meta II. In this manner, three-dimensional structural model coordinates were obtained for Meta II, Meta I, Meta Ib, and Meta $I_{380}$. Of these, the coordinates for Meta II, the structure that binds a full agonist, and for Meta I, the structure that binds an inverse agonist, are shown in Tables 1 and 2, respectively.

Based on the coordinates so obtained, three-dimensional structural models were constructed for complexes bound to chromophore ligands. The structural models for the complexes of Meta II, Meta I, Meta Ib, and Meta $I_{380}$ are shown in FIGS. 3 to 6, respectively.

Lengthy table referenced here

US09069700-20150630-T00001

Please refer to the end of the specification for access instructions.

Lengthy table referenced here

US09069700-20150630-T00002

Please refer to the end of the specification for access instructions.

The Meta II structure constructed here has the arrangement of the extracellular helices very similar to that of bacteriorhodopsin, the crystal structure of which has already been known. The arrangement of the helices of Meta II, however, is significantly different from that of helices of bacteriorhodopsin on the cytoplasmic side.

A method for constructing structural models for complexes of other G protein-coupled proteins formed with respective ligands, as well as a method for constructing three-dimensional structural models for these GPCRs in the structural models for the complexes, will now be described with reference to specific examples using the structural models for the four activated intermediates of rhodopsin: Meta II, Meta I, Meta Ib, and Meta $I_{380}$.

For other GPCRs, inverse agonists, antagonists, partial agonists, and full agonists exist as different compounds. For this reason, the degree of activation can be defined for each receptor conformation that binds each of the ligands. Accordingly, of the structural models of other GPCRs that have been constructed based on the structural models for the photoactivated intermediates of rhodopsin, namely, the four activated intermediates of rhodopsin of the present invention, the structural models for GPCRs of adrenaline, muscarinic acetylcholine, histamine H2, serotonin, and dopamine, for which inverse agonists, antagonists, partial agonists, and full agonists are, known to exist as different compounds, are used as specific examples in studying interactions between the structural models of GPCRs of the present invention and their respective ligands.

This study demonstrates the usefulness and viability of the structural models for GPCRs provided in accordance with the present invention.

(1) Propranolol, an inverse agonist of adrenergic beta-2 receptors, inactivates the receptor completely. The fact that most of the light energy absorbed by rhodopsin is used to generate Meta I suggests that the structure to which an inverse agonist of beta-2 receptor binds has a structure similar to Meta I.

Figure 7:
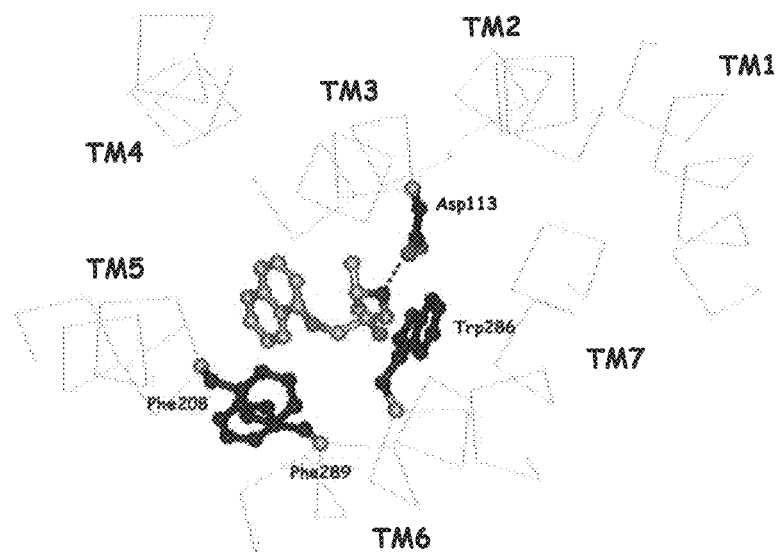
FIG. 7 is a structural model in one embodiment of the present invention showing a complex that an adrenergic beta-2 receptor to serve as a Meta I-like structure of the present invention forms with an inverse agonist propranolol.

A structural model for a complex that propranolol forms with an adrenergic beta-2 receptor is shown in FIG. 7.

The amino group of the ligand interacts with the Asp residue conserved on TM3, whereas the naphthyl group of propranolol forms a cluster of aromatic rings with aromatic amino acid residues of TM5 and TM6. This interaction stabilizes inactive structure of the receptor.

(2) In a complex that an adrenergic beta-2 receptor forms with its full agonist (S)-isoproterenol, the amino group interacts with the Asp residue similarly conserved on TM3.

Meanwhile, the catechol group interacts with the two Ser groups on TM5. This serves as a model for stabilizing the structure of fully activated Meta II-like structures.

Figure 8:
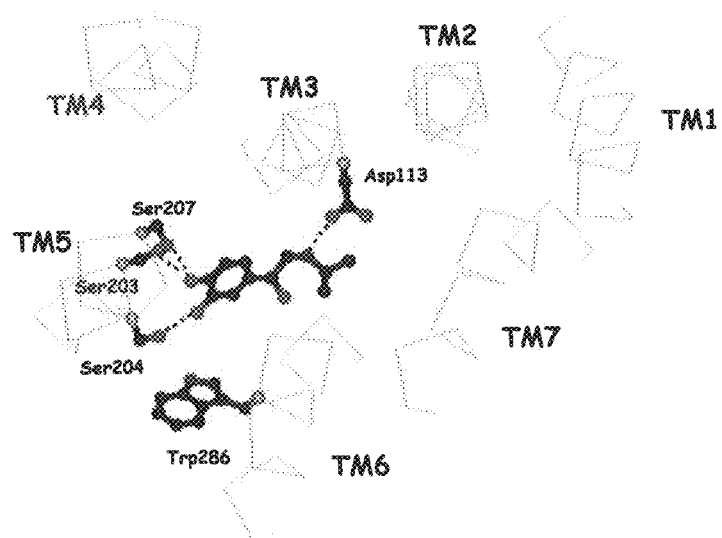
FIG. 8 is a structural model in another embodiment of the present invention showing a complex that an adrenergic beta-2 receptor to serve as a Meta II-like structure of the present invention forms with a full agonist (S)-isoproterenol.

A structural model for the complex formed with (S)-isoproterenol is shown in FIG. 8.

Figure 9:
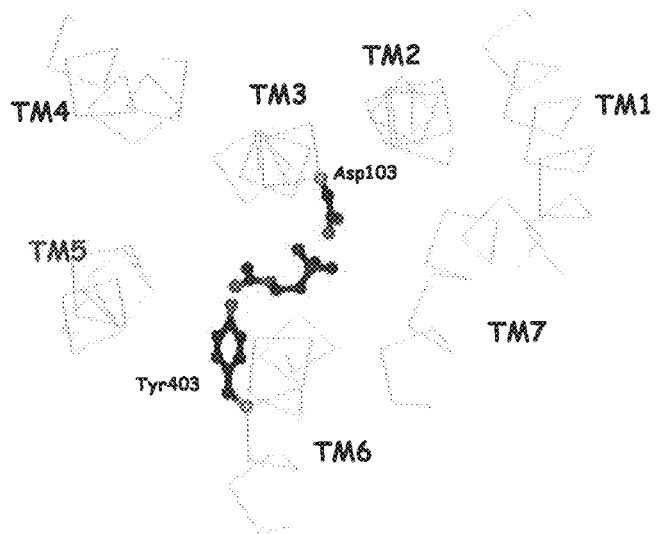
FIG. 9 is a structural model in another embodiment of the present invention showing a complex that a muscarinic acetylcholine receptor to serve as a Meta II-like structure of the present invention forms with a full agonist acetylcholine.

(3) A complex that a muscarinic acetylcholine receptor forms with acetylcholine serves as a typical example of stabilization of Meta II-like structure by a full agonist (FIG. 9).

Cationic moiety of acetylcholine interacts with the Asp103 residue similarly conserved on TM3. The model for complex on the other hand implies the interaction between Tyr403 residue on TM6 and the acetyl group of the ligand. The site-specific mutation of this Tyr residue has been shown to result in a reduced binding activity of acetylcholine.

On the other hand, this mutation does not affect the binding of antagonists, which is consistent with the fact that the Tyr residue cannot interact with the acetyl group in the Meta I-like inactive structural model but is positioned so that it can interact only in the fully active structural model. Thus, it is believed that this interaction contributes to the stabilization of the fully active structure that results from the conformational change of TM6.

Figure 10:
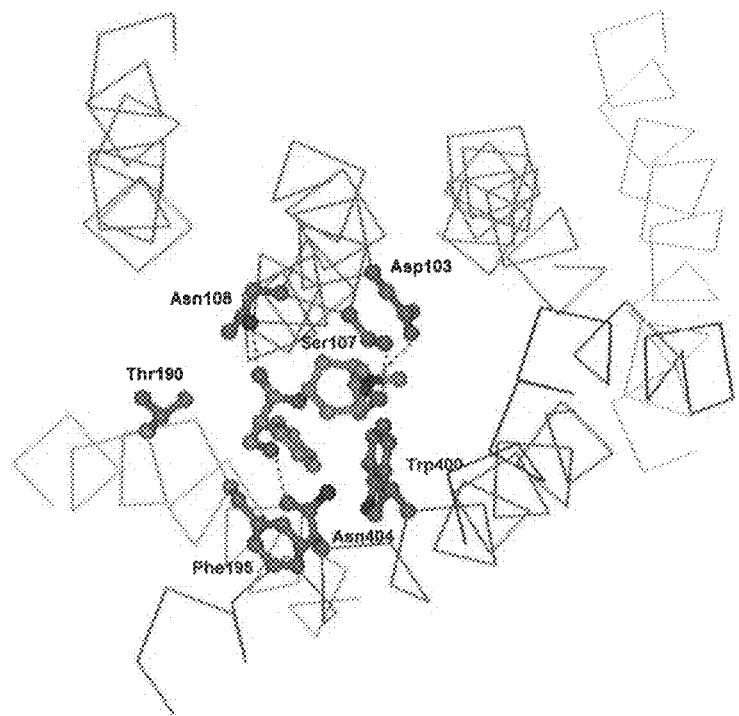
FIG. 10 is a structural model in another embodiment of the present invention showing a complex that a muscarinic acetylcholine receptor to serve as a Meta Ib-like structure of the present invention forms with an antagonist N-methylscopolamine.

(4) On the other hand, an antagonist N-methylscopolamine readily binds the Meta Ib-like inactive structural model and, in particular, binds the Asn404 on TM6 to stabilize the structure bound to the antagonist (FIG. 10).

Figure 11:
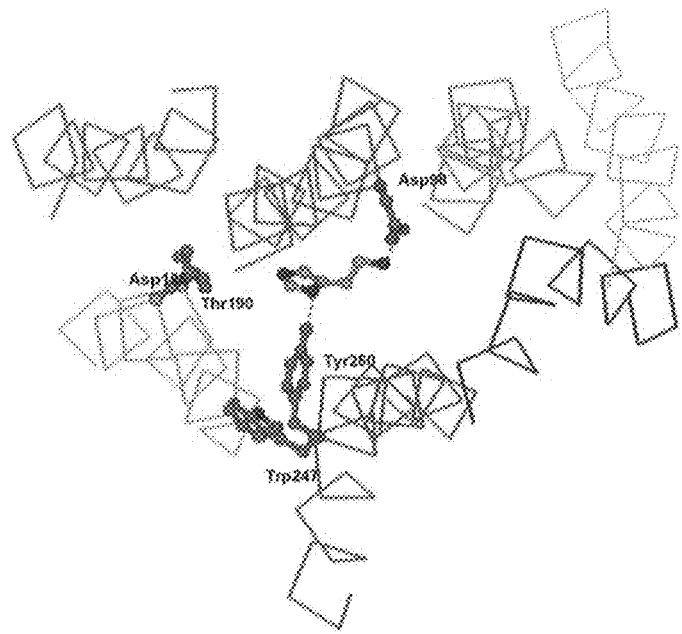
FIG. 11 is a structural model in another embodiment of the present invention showing a complex that a histamine H2 receptor to serve as a Meta II-like structure of the present invention forms with a full agonist histamine.

(5) Likewise, the nitrogen atom of the imidazole group of histamine interacts with the Tyr 250 on TM6 in the Meta II-like structural model (which is present at the same position as the Tyr403 in the muscarinic acetylcholine receptor) of histamine H2 receptor to stabilize the structure bound to the agonist (FIG. 11).

Figure 12:
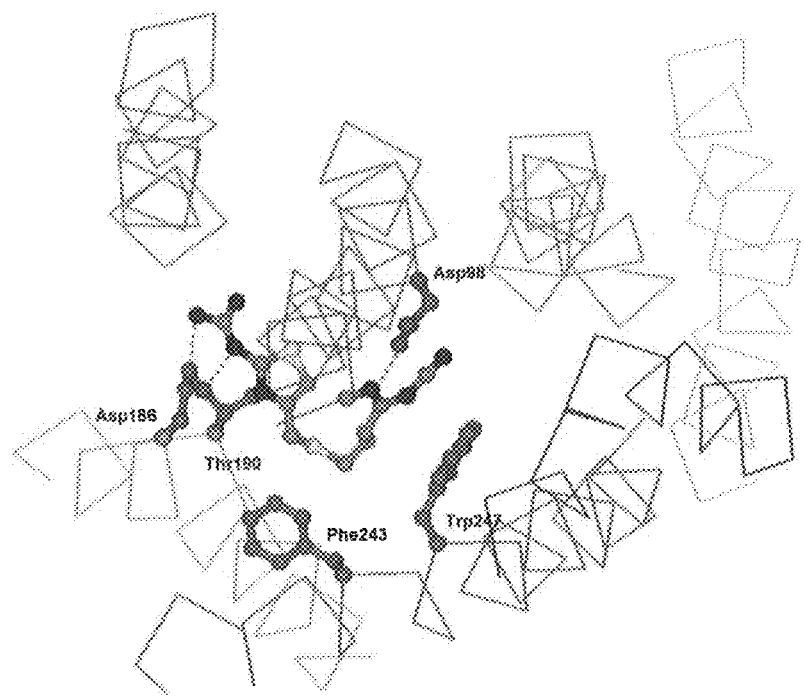
FIG. 12 is a structural model in another embodiment of the present invention showing a complex that a histamine H2 receptor to serve as a Meta Ib-like structure of the present invention forms with an antagonist tiotidine.

(6) On the other hand, tiotidine, an antagonist of the histamine H2 receptor, interacts with the Asp186 on TM5 in the Meta Ib-like structural model to stabilize the structure bound to the antagonist (FIG. 12).

Figure 13:
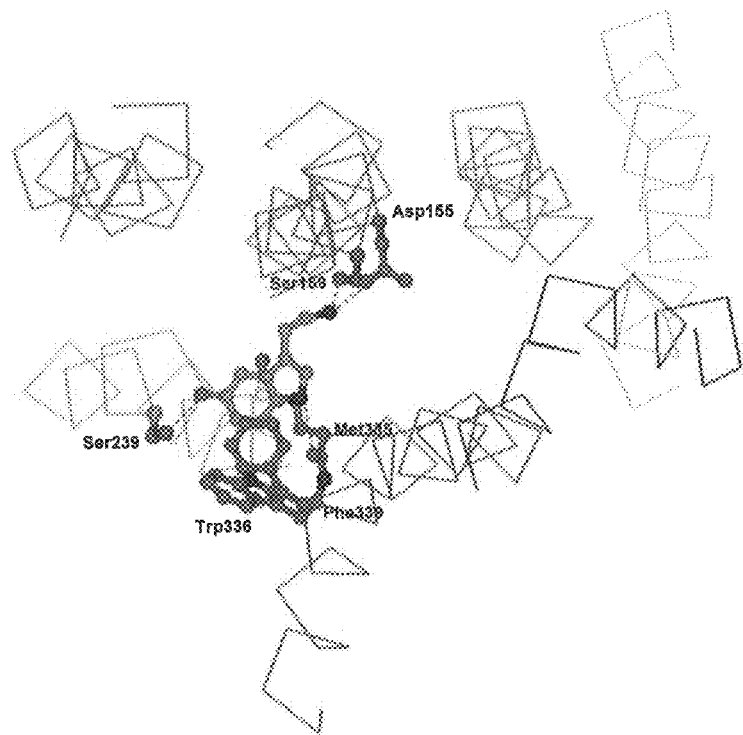
FIG. 13 is a structural model in another embodiment of the present invention showing a complex that a serotonin receptor to serve as a Meta II-like structure of the present invention forms with a full agonist serotonin.

(7) In a model for a serotonin receptor/serotonin complex, NH in the indole backbone, a characteristic functional group of serotonin, interacts with the carbonyl oxygen in the peptide bond of the Met335 on TM6 in the Meta II-like structural model to stabilize the structure bound to the agonist (FIG. 13).

Figure 14:
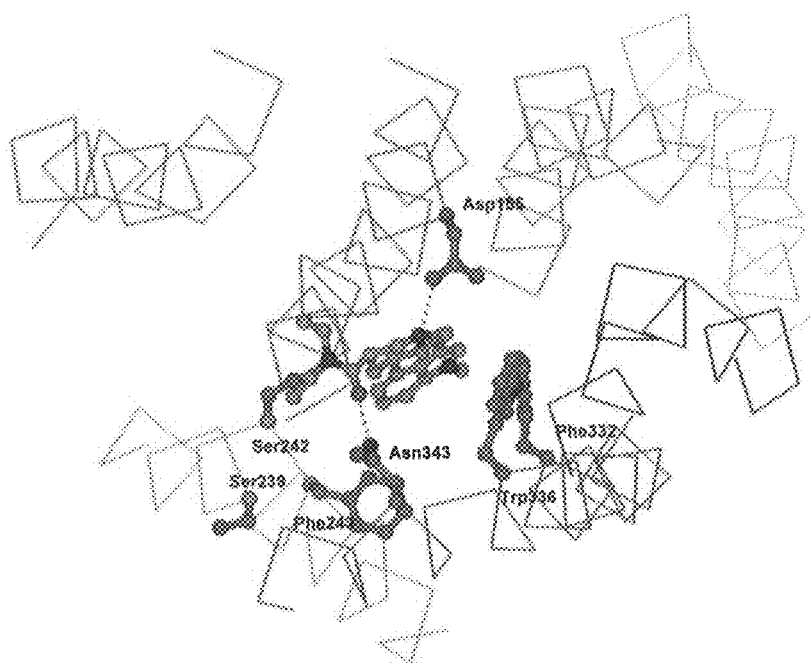
FIG. 14 is a structural model in another embodiment of the present invention showing a complex that a serotonin receptor to serve as a Meta $I_{380}$-like structure of the present invention forms with a partial agonist lysergic acid diethylamide (LSD).

(8) Lysergic acid diethylamide (LSD), known as a partial agonist of serotonin receptors, includes a characteristic diethylamide group, which effectively interacts with the Asn343 of TM6 in the Meta $I_{380}$-like structural model to stabilize the structure bound to the partial agonist. The indole ring of the lysergic acid diethylamide, which is stacked with the highly conserved Trp336 on TM6, also contributes to stabilization of the partial agonist-bound structure. The stacking with tryptophan is unique to the partial agonist-bound structure (FIG. 14).

Figure 15:
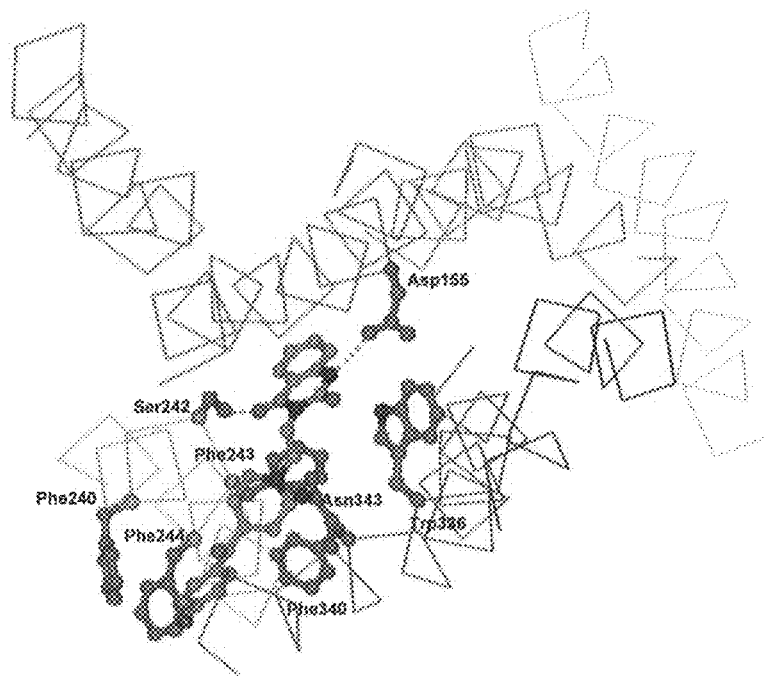
FIG. 15 is a structural model in another embodiment of the present invention showing a complex that a serotonin receptor to serve as a Meta Ib-like structure of the present invention forms with an antagonist ketanserine.

(9) Ketanserine, a serotonin receptor antagonist, interacts both with the Asp155 on TM3 and with Ser242 on TM5 in the Meta Ib-like structural model. This interaction brings about interaction between the amine moiety of the piperidine ring, which is often found in serotonin receptor antagonists such as ketanserine, and the Asn343 on TM6 to stabilize the structure bound to the antagonist (FIG. 15).

Figure 16:
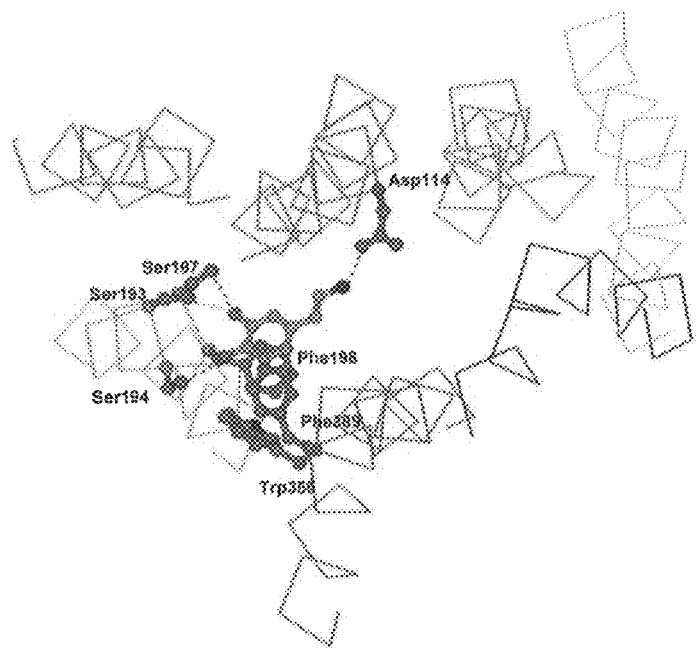
FIG. 16 is a structural model in another embodiment of the present invention showing a complex that a dopamine receptor to serve as a Meta II-like structure of the present invention forms with a full agonist dopamine.

(10) Dopamine receptors bind dopamine at Ser193 and Ser194 on TM5 in the Meta II-like structural model to stabilize the structure bound to the agonist (FIG. 16).

Figure 17:
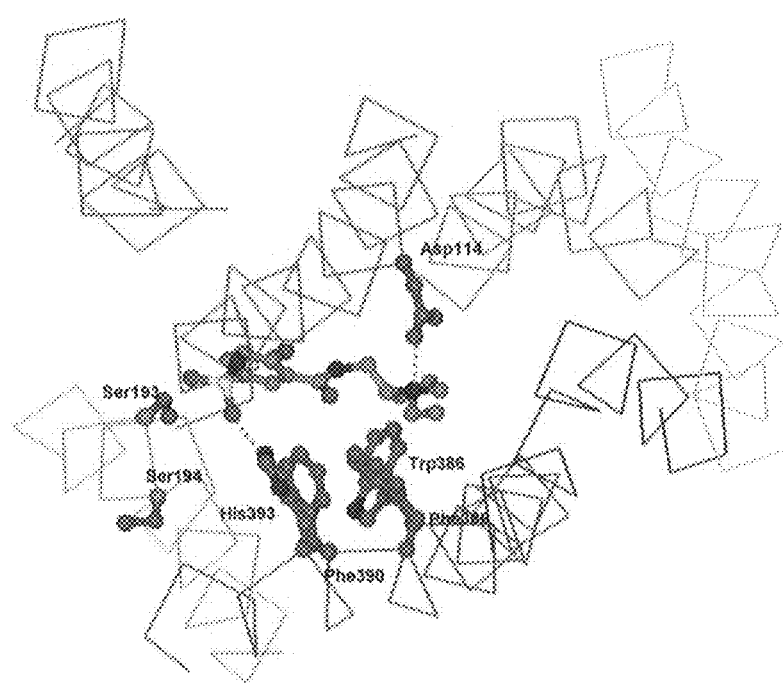
FIG. 17 is a structural model in another embodiment of the present invention showing a complex that a dopamine receptor to serve as a Meta Ib-like structure of the present invention forms with an antagonist sulpiride.
Figure 19:
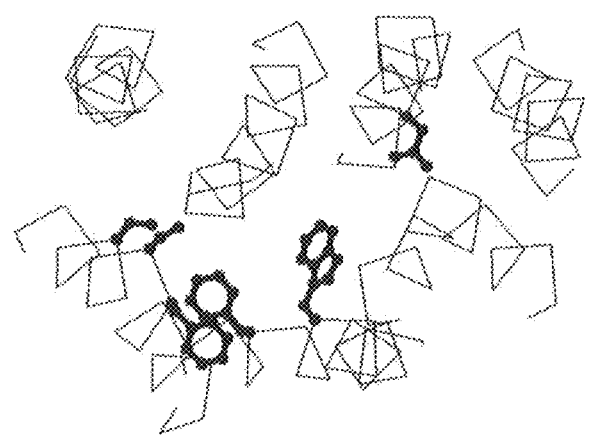
FIG. 19 is a structural model of a human adrenergic alpha-1A receptor bound to an antagonist.
Figure 20:
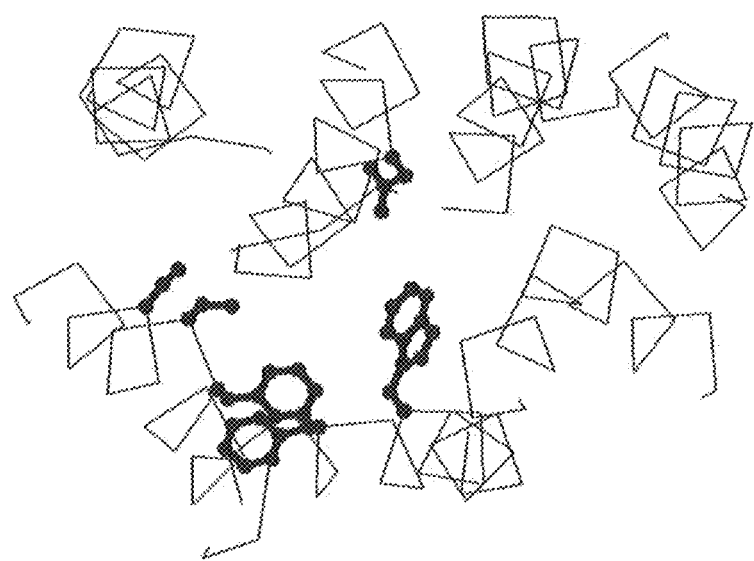
FIG. 20 is a structural model of a human adrenergic alpha-1B receptor bound to an antagonist.
Figure 21:
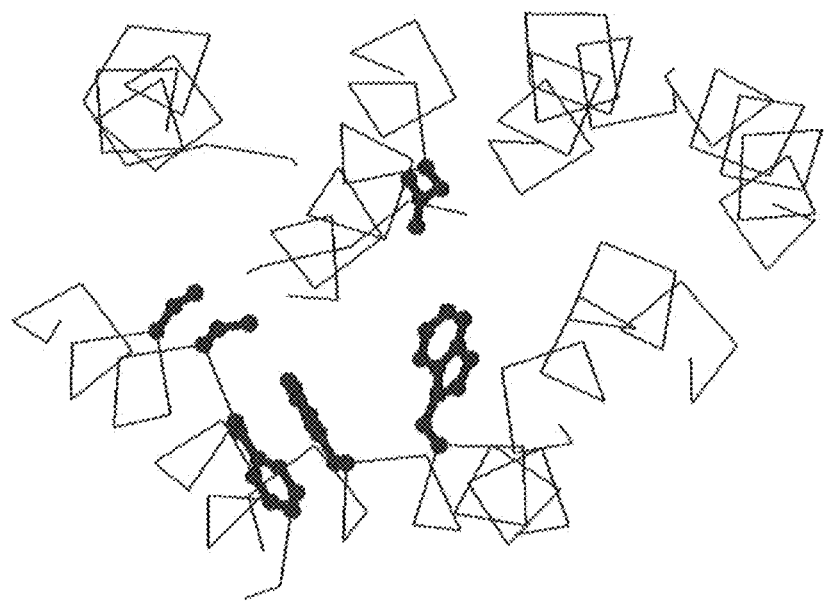
FIG. 21 is a structural model of a human adrenergic alpha-1D receptor bound to an antagonist.
Figure 22:
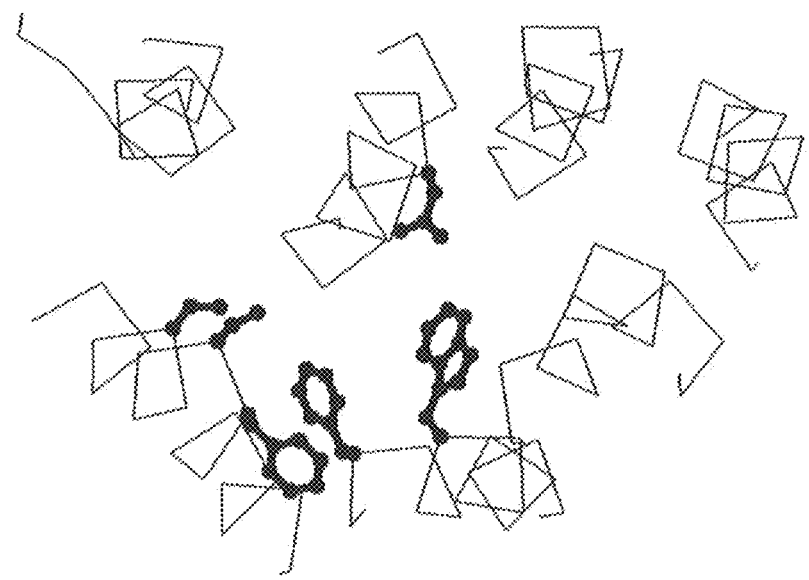
FIG. 22 is a structural model of a human adrenergic alpha-2A receptor bound to an antagonist.
Figure 23:
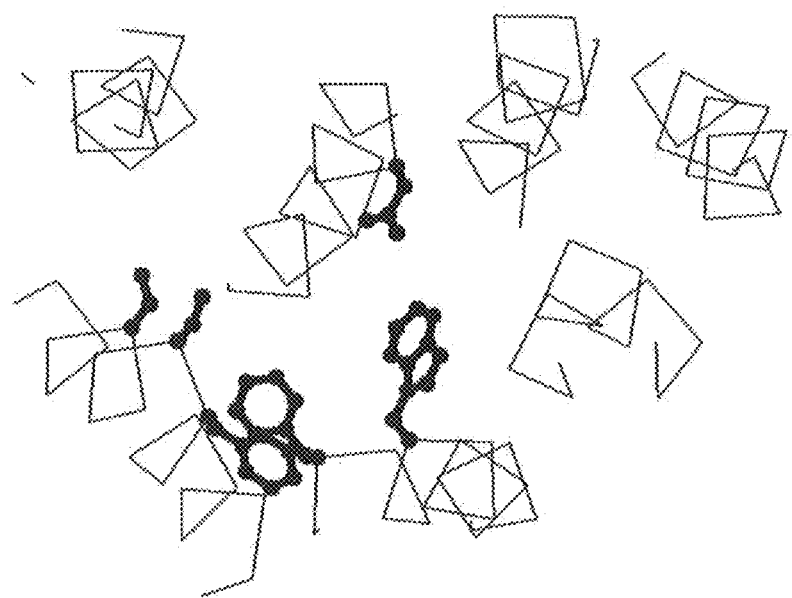
FIG. 23 is a structural model of a human adrenergic alpha-2B receptor bound to an antagonist.
Figure 24:
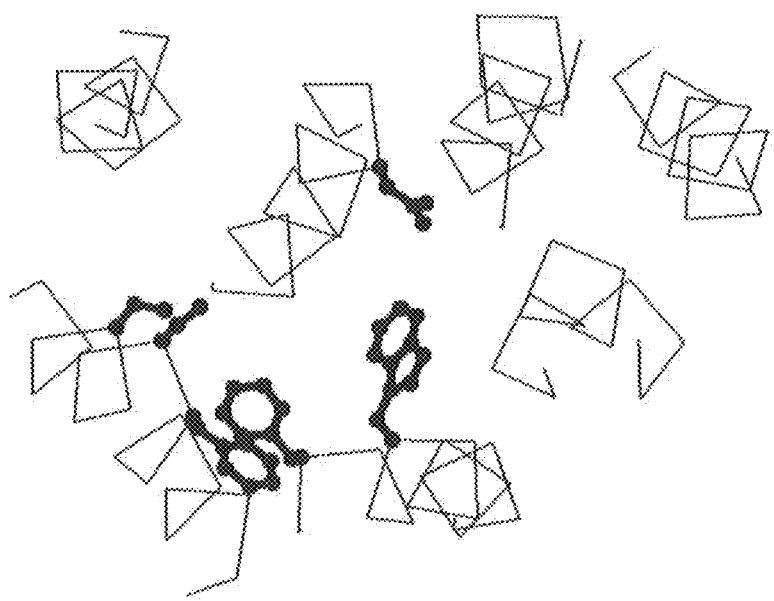
FIG. 24 is a structural model of a human adrenergic alpha-2C-1 receptor bound to an antagonist.
Figure 25:
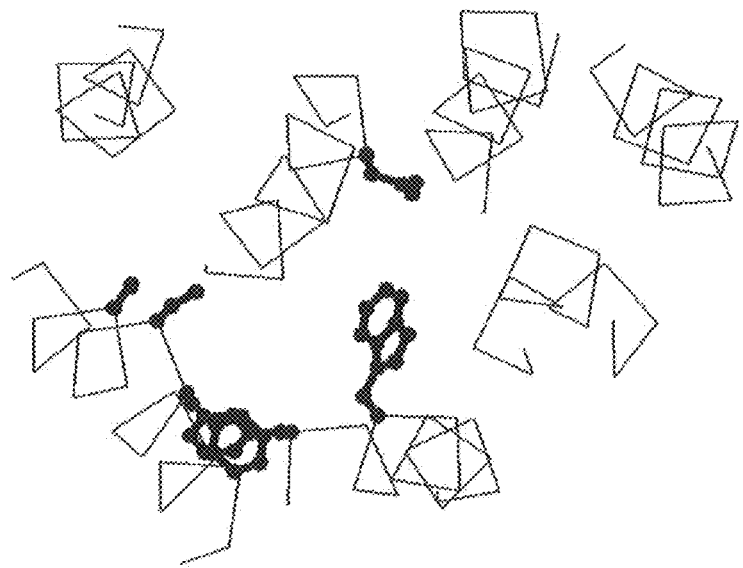
FIG. 25 is a structural model of a human adrenergic alpha-2C-2 receptor bound to an antagonist.
Figure 26:
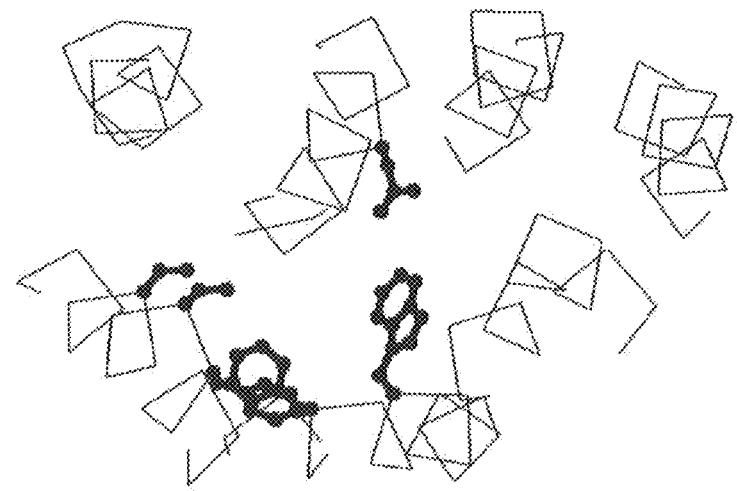
FIG. 26 is a structural model of a human adrenergic beta-1 receptor bound to an antagonist.
Figure 27:
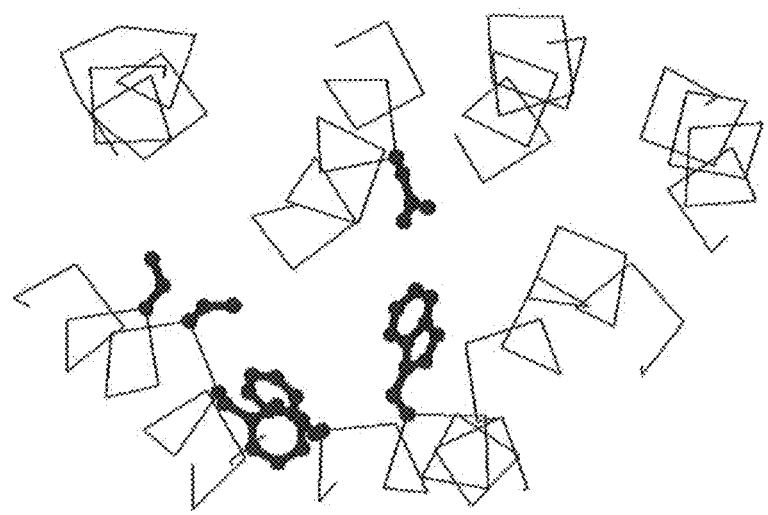
FIG. 27 is a structural model of a human adrenergic beta-2 receptor bound to an antagonist.
Figure 28:
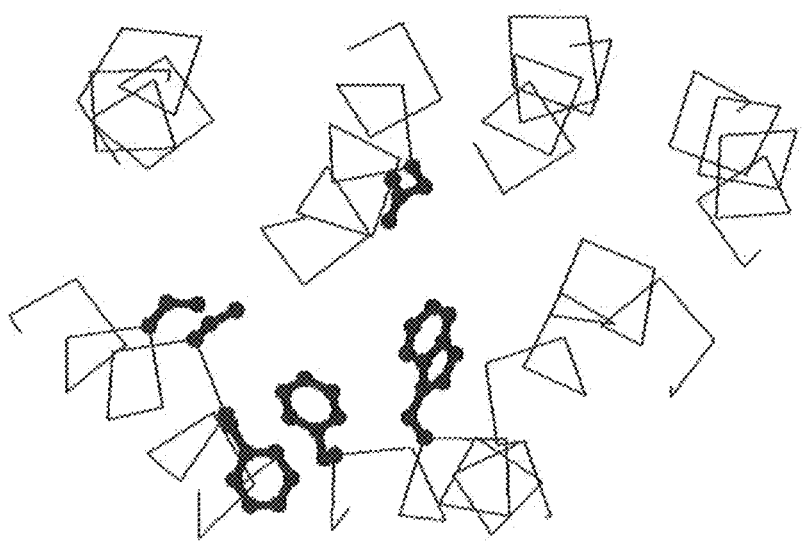
FIG. 28 is a structural model for a human adrenergic alpha-1A receptor isoform 4 bound to an antagonist.
Figure 29:
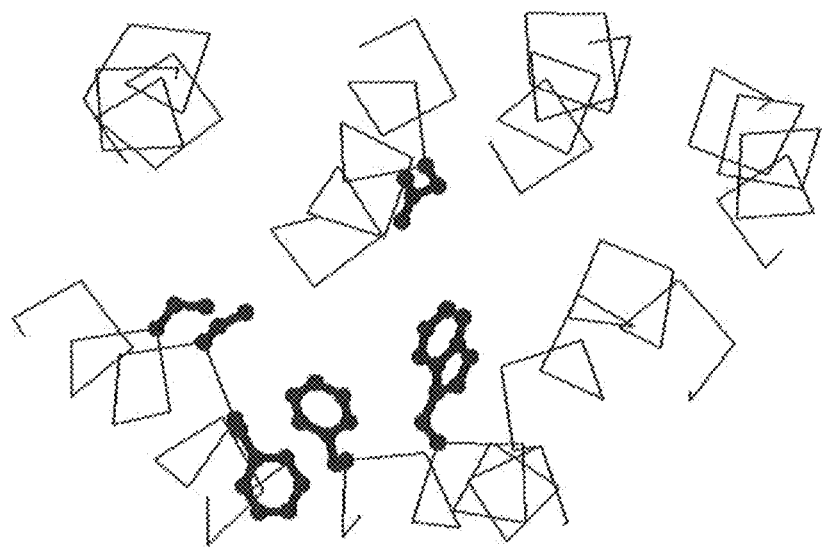
FIG. 29 is a structural model of a human adrenergic alpha-1C receptor isoform 2 bound to an antagonist.
Figure 30:
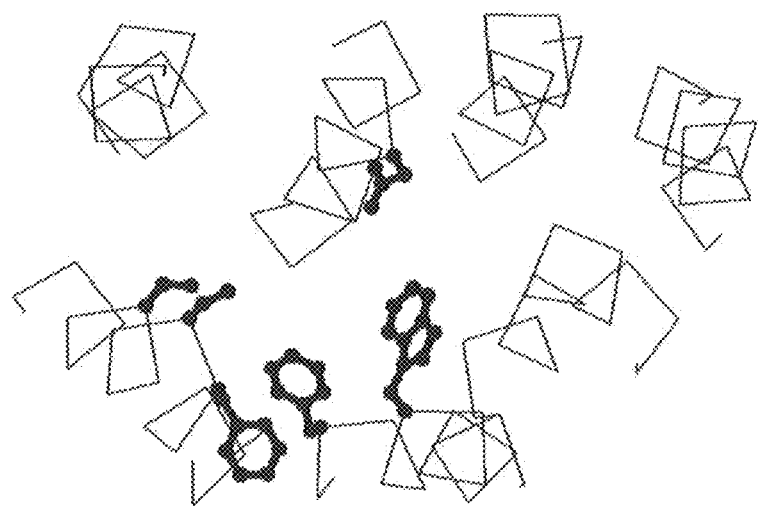
FIG. 30 is a structural model of a human adrenergic alpha-1C receptor isoform 3 bound to an antagonist.
Figure 31:
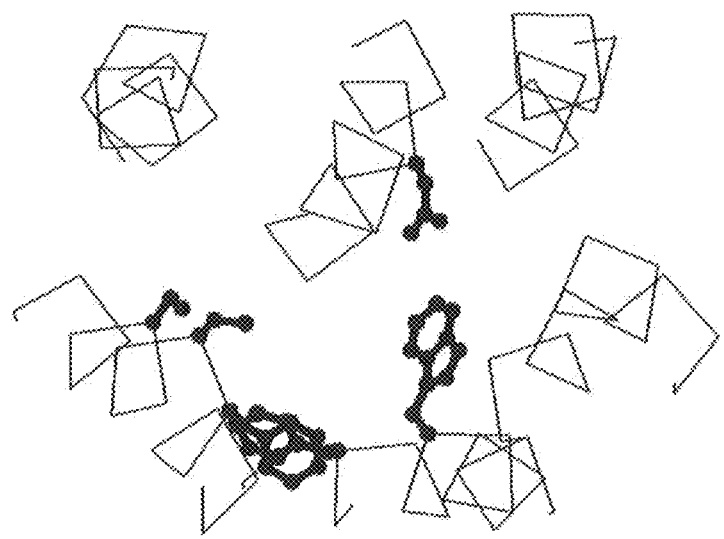
FIG. 31 is a structural model of a human adrenergic alpha-1C-AR receptor bound to an antagonist.

(11) Ligands including a sulfone group, such as sulpiride, which act as antagonists of dopamine receptors, interact with the His393 on TM6 in the Meta Ib-like structural model. This interaction is possible only in the antagonist-bound structure and thus proves to be a major specific interaction with the ligands having sulfone groups (FIG. 17).

As shown in the above-described examples, the structural model for complexes provided in accordance with the present invention allows identification of a set of inverse agonists or full agonists that can stabilize the inactive structure or the fully active structure of the receptor. As for partial agonists, a typical model postulates that they bind both of the inactive and active structures, and the resulting two different complexes exist in equilibrium. However, the fact that mutations on the amino acid residues that specifically bind an antagonist or a full agonist do not affect the activity of partial agonists in either direction implies the presence of a specific receptor structure for this type of ligand. Indeed, it is one of several points that the present invention has demonstrated to be true. Likewise, it appears that inverse agonists also cause the receptors to undergo conformational change from a conformation to bind an antagonist. This also implies the presence of a specific receptor structure, as evidenced by the present invention.

A description will now be given of a method for identifying, screening for, searching for, evaluating or designing a ligand (either an agonist or an antagonist) for a G protein-coupled receptor by the use of either a structural model for the activated intermediates of rhodopsin obtained above or a three-dimensional coordinate for determining such a structural model, or a structural model for a G protein-coupled receptor other than rhodopsin or a three-dimensional coordinate for determining such a structural model.

It should be appreciated that the method described herein is also applicable when it is desired to construct a structural model for a G protein-coupled receptor other than rhodopsin by the use of the structural model for the activated intermediates of rhodopsin or the three-dimensional coordinate for determining such a structural model.

A three-dimensional structural model coordinate is determined for each of the structural models for the intermediates between rhodopsin and Meta II, namely, Meta II, Meta I, Meta Ib, and Meta $I_{380}$. The coordinates are then entered into a computer operated by a computer program capable of displaying three-dimensional structural coordinates of molecules or suitable storage medium for use with such a computer. This allows visual observation or calculation of energy, which are required steps for identifying, screening for, searching for, evaluating, or designing a ligand that binds the above-described receptors to act as an antagonist or an agonist.

Specifically, an agonist or an antagonist can be identified, screened for, searched for, evaluated, or designed for example by examining interactions between ligands and amino acid residues that have specificity to the above-described receptors and are highly conserved among TMs 1 through 7. In particular, compounds that exhibit a higher biological activity and stability than the original ligands that bind GPCRs can be identified, screened for, searched for, evaluated, or designed.

Many of such computer programs for constructing three-dimensional structural coordinates of G protein-coupled receptors are commercially available. These programs typically include means for entering a three-dimensional structural coordinate for a molecule, means for visually displaying the coordinate on a computer screen, means for determining for example distances and bond angles between atoms within the displayed molecule, and means for correcting the coordinate. A program can be also used that includes means for calculating structural energy of a molecule based on the original coordinate of the molecule, and means for calculating free energy by taking into account water molecules and other solvent molecules. In the present invention, a molecule modeling software Insight II-Discover 3 (Molecular Simulations Inc., USA) was used.

One method for identifying, screening for, searching for, evaluating, or designing an agonist or an antagonist provided in accordance with the present invention is executed by entering a three-dimensional structural coordinate of a structural model for Meta II, Meta I, Meta Ib, or Meta $I_{380}$, each of which is a G protein-coupled receptor of the present invention, into a computer or its storage medium, and displaying, by means of a suitable computer program, a three-dimensional structure of the receptor on a computer screen for visual observation.

Specifically, a complex of Meta II structural model and a ligand is displayed on a computer screen. Interactions with amino acid residues specific to the binding of the ligand to the receptor is then observed on the computer screen. The ligand is then chemically or spatially modified and the changes in the local structural coordinate caused by the modification are corrected by determining relative spatial positions of atoms in such a manner that the requirements for chemical bonds are met. In doing so, agonists or antagonists may be selected from a panel of candidates or structures of suitable chemical modification groups displayed on the computer. Alternatively, agonists or antagonists may be designed by calculating chemical modification groups or structures with a low energy state.

According to the present invention, it is also possible to design a receptor mutant and identify, screen for, search for, evaluate or design a ligand capable of binding such a mutant. Since the structural models for the photoactivated intermediates of rhodopsin are considered to correspond to different structures of GPCRs, constructing a three-dimensional structural model for a receptor based on the structure of each intermediate can provide a clue to understand the specificity of binding of further ligands. Furthermore, constructing a three-dimensional structural model for a receptor mutant can provide a clue to understand the specificity of binding of still further ligands.

In designing such a receptor mutant, a complex of, for example, the Meta II structural model and a ligand is displayed on a computer screen in the same manner as described above. Subsequently, amino acid residues involved in the interaction with the ligand, along with amino acid residues in an adjacent region, are displayed on the computer screen. Mutations such as substitutions, deletions and insertions or chemical modifications of one or more amino acid residues are introduced on the computer screen, and the resulting changes in the interactions with the ligand are monitored on the computer screen. The changes in the local structural coordinate caused by the modification are corrected by determining relative spatial positions of atoms in such a manner that the requirements for chemical bonds are met. In doing so, agonists or antagonists may be selected from a panel of candidates or structures of suitable chemical modification groups displayed on the computer. Alternatively, agonists or antagonists may be designed by calculating chemical modification groups or structures with a low energy state.

The receptor mutants so designed can interact more strongly with ligands that act as antagonists or agonists and thus, identifying, scanning for, searching for, evaluating, or designing novel ligands capable of binding the receptor mutant can lead to discovery of compounds that exhibit higher biological activity and stability.

The three-dimensional structural model for GPCRs provided in accordance with the present invention is based on the crystal structure of rhodopsin, or in particular, activated intermediates generated during the photoisomerization reaction of rhodopsin. Each of the activated intermediates exhibits a specificity with which the receptor recognizes a ligand either as an antagonist or as an agonist based on the difference in the position of highly conserved amino acids in helices that play an important role in the interaction with the ligand.

The present invention will now be described in detail with reference to examples, which are not intended to limit the scope of the invention in any way. The scope of the invention is deemed to be defined only by the foregoing description.

Example 1

Construction of Models for Photoactivated Intermediates of Rhodopsin

Using a molecule modeling software Insight II-Discover 3 (Molecular Simulations Inc., USA), a structural model for each of the rhodopsin intermediates was generated and was optimized based on the crystal structure of rhodopsin (Palczewski et al., Science, 289, 144-167, 2000). TM3 was swung about the Cα carbon of Cys110 to serve as the pivot point while the distance to TM2 was kept at 5 Å or more. The magnitude of the swing was determined by taking into consideration the interaction of TM6 with Glu247 for each of Lumi, Meta I, Meta Ib, and Meta $I_{380}$ structures. Specifically, in each of Lumi, Meta I, Meta Ib, and Meta $I_{380}$, Cys140 on TM3 was swung in such a manner that Cys140 is spaced from TM6 by a distance of 1.6 Å, 4.3 Å, 6.8 Å, and 9.0 Å, respectively. Furthermore, N-terminal (Glu150) of the portion of TM4 that would interfere with TM3 was swung toward TM5 about Gly174 on the C-terminal of the helix to serve as the pivot point by a distance of 3.5 Å, 7.4 Å, 12.1 Å, and 17.1 Å, respectively, to avoid interference. The structures so generated were optimized at 300 K by means of molecular kinetics and molecular dynamics so that Cα carbons of the amino acids can be fixed as firmly as possible.

As for the structure of Meta II, TM6 was rotated clockwise by an angle of 100 degrees as viewed from the intracellular side, and the distance between the residues on TM6 and the residues on TM3 was monitored and was decreased to a minimal distance that does not cause steric interference. Upon this, TM5 was twisted about Asn200 in a direction that can avoid steric interference resulting from the rotation of TM6. TM4 was then translated by a distance of 4.1 Å to place it between TM3 and TM5.

As a result, the distance between the Cα-carbon of Cys140 on TM3 and the Cα-carbon of Ala246 on TM6 becomes 12.7

Å and the Cα-carbon of Cys140 on TM3 was positioned at 4.8 Å from Glu150 on TM4. Leu226 on TM5 was positioned at a distance of 10.5 Å from Ala246 on TM6. TM5 and TM4 were moved so that they would not sterically interfere with TM6. The structures so generated were optimized at 300 K by means of molecular kinetics and molecular dynamics so that Cα carbons of the amino acids can be fixed as firmly as possible.

Example 2

Construction of Models for GPCR and GPCR/Ligand Complex

Using the structure of Meta I, Meta Ib, Meta $I_{380}$, and Meta II and based on the homology among the amino acid sequences of rhodopsin and other GPCRs (FIG. 18), three-dimensional conformations for binding a full agonist, a partial agonist, an antagonist, and an inverse agonist were constructed for each of the GPCRs.

For each of the GPCRs, a receptor conformation for binding an inverse agonist was generated by using the structure of Meta I as a template. Using a homology module of Insight II, amino acid substitution was carried out, as were insertion or deletion of amino acid residues in the loop region. Using Discover 3, the conformation was optimized so that the Cα carbon of the amino acids was fixed as firmly as possible.

Likewise, three-dimensional conformations for binding an antagonist, a partial agonist, and a full agonist that correspond to Meta Ib, Meta $I_{380}$, and Meta II, respectively, were constructed for each of the receptors and were optimized.

A ligand corresponding to each conformation of each of the receptors was manually bound to the ligand-binding site of each receptor by using the docking method, such as AUTODOCK, or by mainly forming hydrogen bonds. Using Discover 3, the structure of the resulting complex was optimized on the basis of molecular kinetics and molecular dynamics.

Example 3

Construction of Structural Models for Adrenaline Receptors Bound to Antagonist

Using the structure of rhodopsin Meta Ib as a template, Meta Ib-like structural models of antagonist-bound receptor was constructed for a panel of twelve adrenaline receptors, which form a class of G protein-coupled receptors (GPCRs).

To construct the structural models for the panel of adrenaline receptors, the amino acid sequence of rhodopsin to serve as a template was first aligned with the amino acid sequences of the panel of adrenaline receptors for which to construct the structural model. Clustal W was used as the alignment program (Thompson et al., *Nucleic Acids Research*, 22:4673-4680(1994)). The analysis revealed that while the amino acid sequences showed a relatively low homology to one another, the transmembrane regions, which include conserved hydrophobic residues and sequence motifs, are aligned at a relatively high homology, and the less conserved loop regions tend to include abnormal insertions and deletions.

Thus, the alignment of the regions with low homology was carefully manually corrected by comparing with the three-dimensional structure of rhodopsin to serve as a template and the amino acid sequences of the other GPCRs. As for the intracellular loops, no sequence alignment was made, nor was any model constructed. This is because these regions are diverse among proteins and numerous insertions and deletions make the construction of structural models difficult. Also, these regions are distant from what is considered to be the ligand-binding site and thus are deemed to have no significant influence on the design of, for example, antagonists.

Once constructed, the initial protein structure was refined: Calculations were performed in terms of molecular dynamics and energy minimization with the entire protein except for the regions including insertions and deletions initially fixed and subsequently only each backbone fixed. In this manner, distortions in the initial structure were removed and, as a result, accurate model structure was constructed.

While abnormal loop structure was observed in some of the receptors containing relatively long insertions or deletions, the correction of the alignment improved the accuracy of the structural model to some extent.

For the three-dimensional structure modeling, widely used Modeler program (Accelrys) was employed. Although making alignment is a time-consuming process, the alignment, once completed, can be used repeatedly and thus posed no problem to the modeling process in terms of time required. The time that it took for the modeling itself was approximately one minute for constructing the initial structure for each receptor and approximately 10 minutes for the subsequent refinement process.

FIGS. 19 through 31 show structural models for 12 adrenaline receptors in their antagonist-bound state.

As shown, the peptide backbones of the seven-transmembrane domains, each existing as an α-helix, are shown by solid lines, while the side chains of amino acid residues that are highly conserved among the GPCRs and are involved in the interaction with ligands are shown by ball-and-stick models.

The spatial arrangement of the seven α-helices (transmembrane domains) was identical for each of the structural models of the antagonist-bound 12 adrenaline receptors constructed in this embodiment. The spatial arrangement of the α-helices was also matched in the Meta Ib structure of rhodopsin shown in FIG. 5 and in the different antagonist-bound GPCRs shown in FIG. 10 (N-methylscopolamine), FIG. 12 (tiotidine), FIG. 15 (ketanserine), FIG. 16 (dopamine), and FIG. 17 (sulpiride).

INDUSTRIAL APPLICABILITY

It is expected that G protein-coupled receptors (GPCRs) will account for as much as 5% of the human genome, and, given that those already discovered are included, 2000 or more genes encoding GPCRs will be discovered. It is therefore known that GPCRs are most important and diverse receptors responsible for signal transduction of extracellular information into cells. GPCRs play a crucial role in circulatory systems, central nervous systems, and immune systems and functional impairments of these receptors can lead to various serious diseases. Many drugs are already available and are known to act on these receptors. There is no doubt that the need for the drugs that can control functions of these receptors will be significantly increased in future.

According to the present invention, once the amino acid sequence of a known or a newly discovered GPCR is known, conformations of the receptor to bind full agonists, partial agonists, antagonists, or inverse agonists can be readily generated, and the structure of the ligand-binding site of the receptor provides a clue to create a desired de novo design of ligand and allows screening of a panel of existing compounds for compounds that bind each conformation.

For GPCRs that are orphan receptors, screening for agonists or antagonists relying for example on their functionalities has been particularly difficult due to the absence of the molecules that actually bind the receptors. The receptor structure provided in accordance with the present invention, however, has well-understood functionalities and thus serves as a means to readily find agonists or antagonists. The agonists or the antagonists can then be used to understand the functions of the orphan receptor.

This structure also allows designing constitutively active receptors and thus, screening for ligands using such mutants.

Also, mutations may be introduced at amino acid residues that specifically bind an agonist or an antagonist. This allows binding experiments for screening exclusively for the agonist or the antagonist.

Accordingly, the present invention makes a significant contribution to the development of future pharmaceutical products and serves as a means to develop pharmaceutical products with less side effects.

LENGTHY TABLES

The patent contains a lengthy table section. A copy of the table is available in electronic form from the USPTO web site (http://seqdata.uspto.gov/?pageRequest=docDetail&DocID=US09069700B2). An electronic copy of the table will also be available from the USPTO upon request and payment of the fee set forth in 37 CFR 1.19(b)(3).

The invention claimed is:

1. A method of obtaining structures for active, inactive, and intermediate active forms of rhodopsin for identifying or designing ligands that bind to the intermediate rhodopsin forms comprising:
(a) obtaining three-dimensional structural coordinates for the crystal structure of rhodopsin in the ground state;
(b) pivoting transmembrane helix 3 (TM3) about the Cα carbon of Cys110 such that Cys140 is at a set distance from transmembrane 6 (TM6), while keeping the distance of TM3 to transmembrane helix 2 (TM2) at 5 Å or more, wherein the set distance from TM6 is selected from the group consisting of: 4.3 Å to form activated metarhodopsin I intermediate of rhodopsin, 6.8 Å to form activated metarhodopsin Ib intermediate of rhodopsin, and 9.0 Å to form activated metarhodopsin $I_{380}$ intermediate of rhodopsin;
(c) pivoting transmembrane helix 4 (TM4) about Gly174 such that Glu150 is at a set distance from transmembrane helix 5 (TM5), wherein the set distance from TM5 is selected from the group consisting of: 7.4 Å to form activated metarhodopsin I intermediate of rhodopsin, 12.1 Å to form activated metarhodopsin Ib intermediate of rhodopsin, and 17.1 Å to form activated metarhodopsin $I_{380}$ intermediate of rhodopsin, and wherein the combination of steps (b) and (c) enlarges the ligand binding site by an interaction between Glu134, Arg135, and Try136 on the cytoplasmic side of TM3 and Glu247 on the cytoplasmic side of transmembrane 6 (TM6);
(d) optimizing the structural model of step (c) at 300K by molecular dynamics and energy minimization such that the Cα carbons of the amino acids are fixed, wherein amino acid residues have the same numbering as in bovine rhodopsin, and wherein transmembrane helixes 1, 2, and 7 are not subjected to a conformational change;
(e) optionally further comprising, to form activated metarhodopsin II intermediate of rhodopsin from metarhodopsin I, metarhodopsin Ib, or metarhodopsin $I_{380}$ intermediate of rhodopsin:
 (i) rotating TM6 clockwise by an angle 100 degrees as viewed from the intracellular side; and
 (ii) decreasing the distance between the residues of TM6 and the residues of TM3 to a minimal distance that does not cause steric interference;
 (iii) twisting TM5 about Asn200 to avoid steric interference resulting from said rotation of TM6;
 (iv) translating TM4 by 4.1 Å to place it between TM3 and TM5, thereby placing the Cα-carbon of Cys140 12.7 Å from the Cα-carbon of Ala246 on TM6 and 4.8 Å from Glu150 on TM4, and placing Leu226 on TM5 10.5 Å from Alu246 on TM6;
 (v) moving TM5 and TM4 to a distance that does not cause steric interference with TM6; and
 (vi) optimizing the structural model of step (v) at 300K by molecular dynamics and energy minimization such that the Cα carbons of the amino acids are fixed, wherein amino acid residues have the same numbering as in bovine rhodopsin, and wherein transmembrane helixes 1, 2, and 7 are not subjected to a conformational change; and
(f) binding a previously identified or designed ligand to the activated metarhodopsin I, metarhodopsin Ib, metarhodopsin $I_{380}$, or metarhodopsin II intermediate of rhodopsin to form a complex of the ligand and the activated intermediate of rhodopsin.

2. The method of claim 1, wherein steps (a)-(d) are performed to form metarhodopsin I.

3. The method of claim 2, further comprising the step of determining if the ligand acts as an agonist or antagonist to rhodopsin and binds an activated metarhodopsin I.

4. The method of claim 1, wherein steps (a)-(d) are performed to form metarhodopsin Ib.

5. The method of claim 4, further comprising the step of determining if the ligand acts as an agonist or antagonist to rhodopsin and binds an activated metarhodopsin Ib.

6. The method of claim 1, wherein steps (a)-(d) are performed to form metarhodopsin $I_{380}$.

7. The method of claim 6, further comprising the step of determining if the ligand acts as an agonist or antagonist to rhodopsin and binds an activated metarhodopsin $I_{380}$.

8. The method of claim 1, wherein steps (a)-(e) are performed to form metarhodopsin II.

9. The method of claim 8, further comprising the step of determining if the ligand acts as an agonist or antagonist to rhodopsin and binds an activated metarhodopsin II.

* * * * *

```
                              SEQUENCE LISTING

<160> NUMBER OF SEQ ID NOS: 42

<210> SEQ ID NO 1
<211> LENGTH: 31
<212> TYPE: PRT
<213> ORGANISM: Homo sapiens
<220> FEATURE:
<221> NAME/KEY: TRANSMEM
<222> LOCATION: (1)..(31)
<223> OTHER INFORMATION: human muscarinic acetylcholine m2 receptor
      TM 1

<400> SEQUENCE: 1

Phe Glu Val Val Phe Ile Val Leu Val Ala Ala Ser Leu Ser Leu Val
 1               5                  10                  15

Thr Ile Ile Gly Asn Ile Leu Val Met Val Ser Ile Lys Val Asn
            20                  25                  30

<210> SEQ ID NO 2
<211> LENGTH: 31
<212> TYPE: PRT
<213> ORGANISM: Homo sapiens
<220> FEATURE:
<221> NAME/KEY: TRANSMEM
<222> LOCATION: (1)..(31)
<223> OTHER INFORMATION: human histamine H2 receptor TM 1

<400> SEQUENCE: 2

Ala Cys Lys Ile Thr Ile Thr Val Val Leu Ala Val Leu Ile Leu Ile
 1               5                  10                  15

Thr Val Ala Gly Asn Val Val Val Cys Leu Ala Val Gly Leu Asn
            20                  25                  30

<210> SEQ ID NO 3
<211> LENGTH: 31
<212> TYPE: PRT
<213> ORGANISM: Homo sapiens
<220> FEATURE:
<221> NAME/KEY: TRANSMEM
<222> LOCATION: (1)..(31)
<223> OTHER INFORMATION: human serotonin 5HT2A receptor TM 1

<400> SEQUENCE: 3

Gln Glu Lys Asn Trp Ser Ala Leu Leu Thr Ala Val Val Ile Ile Leu
 1               5                  10                  15
```

```
Thr Ile Ala Ala Asn Ile Leu Val Ile Met Ala Val Ser Leu Glu
            20                  25                  30

<210> SEQ ID NO 4
<211> LENGTH: 31
<212> TYPE: PRT
<213> ORGANISM: Homo sapiens
<220> FEATURE:
<221> NAME/KEY: TRANSMEM
<222> LOCATION: (1)..(31)
<223> OTHER INFORMATION: human dopamine D2 receptor TM 1

<400> SEQUENCE: 4

Pro His Tyr Asn Tyr Tyr Ala Thr Leu Leu Thr Leu Leu Ile Ala Val
 1               5                  10                  15

Ile Val Phe Gly Asn Val Leu Val Cys Met Ala Val Ser Arg Glu
            20                  25                  30

<210> SEQ ID NO 5
<211> LENGTH: 31
<212> TYPE: PRT
<213> ORGANISM: Homo sapiens
<220> FEATURE:
<221> NAME/KEY: TRANSMEM
<222> LOCATION: (1)..(31)
<223> OTHER INFORMATION: human adrenergic b2 receptor TM 1

<400> SEQUENCE: 5

Val Trp Val Val Gly Met Gly Ile Val Met Ser Leu Ile Val Leu Ala
 1               5                  10                  15

Ile Val Phe Gly Asn Val Leu Val Ile Thr Ala Ile Ala Lys Phe
            20                  25                  30

<210> SEQ ID NO 6
<211> LENGTH: 31
<212> TYPE: PRT
<213> ORGANISM: Homo sapiens
<220> FEATURE:
<221> NAME/KEY: TRANSMEM
<222> LOCATION: (1)..(31)
<223> OTHER INFORMATION: human rhodopsin TM 1

<400> SEQUENCE: 6

Trp Gln Phe Ser Met Leu Ala Ala Tyr Met Phe Leu Leu Ile Met Leu
 1               5                  10                  15

Gly Phe Pro Ile Asn Phe Leu Thr Leu Tyr Val Thr Val Gln His
            20                  25                  30

<210> SEQ ID NO 7
<211> LENGTH: 30
<212> TYPE: PRT
<213> ORGANISM: Homo sapiens
<220> FEATURE:
<221> NAME/KEY: TRANSMEM
<222> LOCATION: (1)..(30)
<223> OTHER INFORMATION: human muscarinic acetylcholine m2 receptor TM 2

<400> SEQUENCE: 7

Val Asn Asn Tyr Phe Leu Phe Ser Leu Ala Cys Ala Asp Leu Ile Ile
 1               5                  10                  15

Gly Val Phe Ser Met Asn Leu Tyr Thr Leu Tyr Thr Val Ile
            20                  25                  30

<210> SEQ ID NO 8
<211> LENGTH: 30
<212> TYPE: PRT
```

```
<213> ORGANISM: Homo sapiens
<220> FEATURE:
<221> NAME/KEY: TRANSMEM
<222> LOCATION: (1)..(30)
<223> OTHER INFORMATION: human histamine H2 receptor TM 2

<400> SEQUENCE: 8

Leu Thr Asn Cys Phe Ile Val Ser Leu Ala Ile Thr Asp Leu Leu
 1               5                  10                  15

Gly Leu Leu Val Leu Pro Phe Ser Ala Ile Tyr Gln Leu Ser
            20                  25                  30

<210> SEQ ID NO 9
<211> LENGTH: 30
<212> TYPE: PRT
<213> ORGANISM: Homo sapiens
<220> FEATURE:
<221> NAME/KEY: TRANSMEM
<222> LOCATION: (1)..(30)
<223> OTHER INFORMATION: human serotonin 5HT2A receptor TM 2

<400> SEQUENCE: 9

Ala Thr Asn Tyr Phe Leu Met Ser Leu Ala Ile Ala Asp Met Leu Leu
 1               5                  10                  15

Gly Phe Leu Val Met Pro Val Ser Met Leu Thr Ile Leu Tyr
            20                  25                  30

<210> SEQ ID NO 10
<211> LENGTH: 21
<212> TYPE: PRT
<213> ORGANISM: Homo sapiens
<220> FEATURE:
<221> NAME/KEY: TRANSMEM
<222> LOCATION: (1)..(21)
<223> OTHER INFORMATION: human dopamine D2 receptor TM 2

<400> SEQUENCE: 10

Thr Thr Asn Tyr Val Ser Ala Val Ala Asp Val Ala Thr Val Met Trp
 1               5                  10                  15

Val Val Tyr Val Val
            20

<210> SEQ ID NO 11
<211> LENGTH: 30
<212> TYPE: PRT
<213> ORGANISM: Homo sapiens
<220> FEATURE:
<221> NAME/KEY: TRANSMEM
<222> LOCATION: (1)..(30)
<223> OTHER INFORMATION: human adrenergic b2 receptor TM 2

<400> SEQUENCE: 11

Val Thr Asn Tyr Phe Ile Thr Ser Leu Ala Cys Ala Asp Leu Val Met
 1               5                  10                  15

Gly Leu Ala Val Val Pro Phe Gly Ala Ala His Ile Leu Met
            20                  25                  30

<210> SEQ ID NO 12
<211> LENGTH: 30
<212> TYPE: PRT
<213> ORGANISM: Homo sapiens
<220> FEATURE:
<221> NAME/KEY: TRANSMEM
<222> LOCATION: (1)..(30)
<223> OTHER INFORMATION: human rhodopsin TM 2

<400> SEQUENCE: 12
```

Pro Leu Asn Tyr Ile Leu Leu Asn Leu Ala Val Ala Asp Leu Phe Met
1               5                   10                  15

Val Phe Gly Gly Phe Thr Thr Thr Leu Tyr Thr Ser Leu His
            20                  25                  30

<210> SEQ ID NO 13
<211> LENGTH: 35
<212> TYPE: PRT
<213> ORGANISM: Homo sapiens
<220> FEATURE:
<221> NAME/KEY: TRANSMEM
<222> LOCATION: (1)..(35)
<223> OTHER INFORMATION: human muscarinic acetylcholine m2 receptor TM 3

<400> SEQUENCE: 13

Gly Pro Val Val Cys Asp Leu Trp Leu Ala Leu Asp Tyr Val Val Ser
1               5                   10                  15

Asn Ala Ser Val Met Asn Leu Leu Ile Ile Ser Phe Asp Arg Tyr Phe
            20                  25                  30

Cys Val Thr
        35

<210> SEQ ID NO 14
<211> LENGTH: 35
<212> TYPE: PRT
<213> ORGANISM: Homo sapiens
<220> FEATURE:
<221> NAME/KEY: TRANSMEM
<222> LOCATION: (1)..(35)
<223> OTHER INFORMATION: human histamine H2 receptor TM 3

<400> SEQUENCE: 14

Gly Lys Val Phe Cys Asn Ile Tyr Thr Ser Leu Asp Val Met Leu Cys
1               5                   10                  15

Thr Ala Ser Ile Leu Asn Leu Phe Met Ile Ser Leu Asp Arg Tyr Cys
            20                  25                  30

Ala Val Met
        35

<210> SEQ ID NO 15
<211> LENGTH: 35
<212> TYPE: PRT
<213> ORGANISM: Homo sapiens
<220> FEATURE:
<221> NAME/KEY: TRANSMEM
<222> LOCATION: (1)..(35)
<223> OTHER INFORMATION: human serotonin 5HT2A receptor TM 3

<400> SEQUENCE: 15

Pro Ser Lys Leu Cys Ala Val Trp Ile Tyr Leu Asp Val Leu Phe Ser
1               5                   10                  15

Thr Ala Ser Ile Met His Leu Cys Ala Ile Ser Leu Asp Arg Tyr Val
            20                  25                  30

Ala Ile Gln
        35

<210> SEQ ID NO 16
<211> LENGTH: 35
<212> TYPE: PRT
<213> ORGANISM: Homo sapiens
<220> FEATURE:
<221> NAME/KEY: TRANSMEM
<222> LOCATION: (1)..(35)
<223> OTHER INFORMATION: human dopamine D2 receptor TM 3

```
<400> SEQUENCE: 16

Ser Arg Ile His Cys Asp Ile Phe Val Thr Leu Asp Val Met Met Cys
1               5                   10                  15

Thr Ala Ser Ile Leu Asn Leu Cys Ala Ile Ser Ile Asp Arg Tyr Thr
                20                  25                  30

Ala Val Ala
        35

<210> SEQ ID NO 17
<211> LENGTH: 35
<212> TYPE: PRT
<213> ORGANISM: Homo sapiens
<220> FEATURE:
<221> NAME/KEY: TRANSMEM
<222> LOCATION: (1)..(35)
<223> OTHER INFORMATION: human adrenergic b2 receptor TM 3

<400> SEQUENCE: 17

Gly Asn Phe Trp Cys Glu Phe Trp Thr Ser Ile Asp Val Leu Cys Val
1               5                   10                  15

Thr Ala Ser Ile Glu Thr Leu Cys Val Ile Ala Val Asp Arg Tyr Phe
                20                  25                  30

Ala Ile Thr
        35

<210> SEQ ID NO 18
<211> LENGTH: 35
<212> TYPE: PRT
<213> ORGANISM: Homo sapiens
<220> FEATURE:
<221> NAME/KEY: TRANSMEM
<222> LOCATION: (1)..(35)
<223> OTHER INFORMATION: human rhodopsin TM 3

<400> SEQUENCE: 18

Gly Pro Thr Gly Cys Asn Leu Glu Gly Phe Phe Ala Thr Leu Gly Gly
1               5                   10                  15

Glu Ile Ala Leu Trp Ser Leu Val Val Leu Ala Ile Glu Arg Tyr Val
                20                  25                  30

Val Val Cys
        35

<210> SEQ ID NO 19
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human muscarinic acetylcholine m2 receptor TM 4

<400> SEQUENCE: 19

Arg Thr Thr Lys Met Ala Gly Met Met Ile Ala Ala Ala Trp Val Leu
1               5                   10                  15

Ser Phe Ile Leu Trp Ala Pro Ala Ile Leu
                20                  25

<210> SEQ ID NO 20
<211> LENGTH: 26
<212> TYPE: PRT
<213> ORGANISM: Homo sapiens
<220> FEATURE:
<221> NAME/KEY: TRANSMEM
```

```
<222> LOCATION: (1)..(26)
<223> OTHER INFORMATION: human histamine H2 receptor TM 4

<400> SEQUENCE: 20

Val Thr Pro Val Arg Val Ala Ile Ser Leu Val Leu Ile Trp Val Ile
 1               5                  10                  15

Ser Ile Thr Leu Ser Phe Leu Ser Ile His
            20                  25

<210> SEQ ID NO 21
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human serotonin 5HT2A receptor TM 4

<400> SEQUENCE: 21

Asn Ser Arg Thr Lys Ala Phe Leu Lys Ile Ile Ala Val Trp Thr Ile
 1               5                  10                  15

Ser Val Gly Ile Ser Met Pro Ile Pro Val
            20                  25

<210> SEQ ID NO 22
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human dopamine D2 receptor TM 4

<400> SEQUENCE: 22

Ser Ser Lys Arg Arg Val Thr Val Met Ile Ser Ile Val Trp Val Leu
 1               5                  10                  15

Ser Phe Thr Ile Ser Cys Pro Leu Leu Phe
            20                  25

<210> SEQ ID NO 23
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human adrenergic b2 receptor TM 4

<400> SEQUENCE: 23

Leu Thr Lys Asn Lys Ala Arg Val Ile Ile Leu Met Val Trp Ile Val
 1               5                  10                  15

Ser Gly Leu Thr Ser Phe Leu Pro Ile Gln
            20                  25

<210> SEQ ID NO 24
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human rhodopsin TM 4

<400> SEQUENCE: 24

Phe Gly Glu Asn His Ala Ile Met Gly Val Ala Phe Thr Trp Val Met
 1               5                  10                  15
```

```
Ala Leu Ala Cys Ala Ala Pro Pro Leu Val
            20                  25

<210> SEQ ID NO 25
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human muscarinic acetylcholine m2 receptor TM 5

<400> SEQUENCE: 25

Ala Ala Val Thr Phe Gly Thr Ala Ile Ala Ala Phe Tyr Leu Pro Val
  1               5                  10                  15

Ile Ile Met Thr Val Leu Tyr Trp His Ile
            20                  25

<210> SEQ ID NO 26
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human histamine H2 receptor TM 5

<400> SEQUENCE: 26

Glu Val Tyr Gly Leu Val Asp Gly Leu Val Thr Phe Tyr Leu Pro Leu
  1               5                  10                  15

Leu Ile Met Cys Ile Thr Tyr Tyr Arg Ile
            20                  25

<210> SEQ ID NO 27
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human serotonin 5HT2A receptor TM 5

<400> SEQUENCE: 27

Asp Asn Phe Val Leu Ile Gly Ser Phe Val Ser Phe Phe Ile Pro Leu
  1               5                  10                  15

Thr Ile Met Val Ile Thr Tyr Phe Leu Thr
            20                  25

<210> SEQ ID NO 28
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human dopamine D2 receptor TM 5

<400> SEQUENCE: 28

Pro Ala Phe Val Val Tyr Ser Ser Ile Val Ser Phe Tyr Val Pro Phe
  1               5                  10                  15

Ile Val Thr Leu Leu Val Tyr Ile Lys Ile
            20                  25

<210> SEQ ID NO 29
<211> LENGTH: 26
```

```
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human adrenergic b2 receptor TM 5

<400> SEQUENCE: 29

Gln Ala Tyr Ala Ile Ala Ser Ser Ile Val Ser Phe Tyr Val Pro Leu
  1               5                  10                  15

Val Ile Met Val Phe Val Tyr Ser Arg Val
             20                  25

<210> SEQ ID NO 30
<211> LENGTH: 26
<212> TYPE: PRT
<213> ORGANISM: Homo sapiens
<220> FEATURE:
<221> NAME/KEY: TRANSMEM
<222> LOCATION: (1)..(26)
<223> OTHER INFORMATION: human rhodopsin TM 5

<400> SEQUENCE: 30

Glu Ser Phe Val Ile Tyr Met Phe Val Val His Phe Ile Ile Pro Leu
  1               5                  10                  15

Ile Val Ile Phe Phe Cys Tyr Gly Gln Leu
             20                  25

<210> SEQ ID NO 31
<211> LENGTH: 36
<212> TYPE: PRT
<213> ORGANISM: Homo sapiens
<220> FEATURE:
<221> NAME/KEY: TRANSMEM
<222> LOCATION: (1)..(36)
<223> OTHER INFORMATION: human muscarinic acetylcholine m2 receptor TM 6

<400> SEQUENCE: 31

Pro Pro Ser Arg Glu Lys Lys Val Thr Arg Thr Ile Leu Ala Ile Leu
  1               5                  10                  15

Leu Ala Phe Ile Ile Thr Trp Ala Pro Tyr Asn Val Met Val Leu Ile
             20                  25                  30

Asn Thr Phe Cys
         35

<210> SEQ ID NO 32
<211> LENGTH: 36
<212> TYPE: PRT
<213> ORGANISM: Homo sapiens
<220> FEATURE:
<221> NAME/KEY: TRANSMEM
<222> LOCATION: (1)..(36)
<223> OTHER INFORMATION: human histamine H2 receptor TM 6

<400> SEQUENCE: 32

Ala Thr Ile Arg Glu His Lys Ala Thr Val Thr Leu Ala Ala Val Met
  1               5                  10                  15

Gly Ala Phe Ile Ile Cys Trp Phe Pro Tyr Phe Thr Ala Phe Val Tyr
             20                  25                  30

Arg Gly Leu Arg
         35

<210> SEQ ID NO 33
<211> LENGTH: 36
<212> TYPE: PRT
```

```
<213> ORGANISM: Homo sapiens
<220> FEATURE:
<221> NAME/KEY: TRANSMEM
<222> LOCATION: (1)..(36)
<223> OTHER INFORMATION: human serotonin 5HT2A receptor TM 6

<400> SEQUENCE: 33

Ser Ile Ser Asn Glu Gln Lys Ala Cys Lys Val Leu Gly Ile Val Phe
 1               5                  10                  15

Phe Leu Phe Val Val Met Trp Cys Pro Phe Phe Ile Thr Asn Ile Met
                20                  25                  30

Ala Val Ile Cys
            35

<210> SEQ ID NO 34
<211> LENGTH: 36
<212> TYPE: PRT
<213> ORGANISM: Homo sapiens
<220> FEATURE:
<221> NAME/KEY: TRANSMEM
<222> LOCATION: (1)..(36)
<223> OTHER INFORMATION: human dopamine D2 receptor TM 6

<400> SEQUENCE: 34

Ser Gln Gln Lys Glu Lys Lys Ala Thr Gln Met Leu Ala Ile Val Leu
 1               5                  10                  15

Gly Val Phe Ile Ile Cys Trp Leu Pro Phe Phe Ile Thr His Ile Leu
                20                  25                  30

Asn Ile His Cys
            35

<210> SEQ ID NO 35
<211> LENGTH: 36
<212> TYPE: PRT
<213> ORGANISM: Homo sapiens
<220> FEATURE:
<221> NAME/KEY: TRANSMEM
<222> LOCATION: (1)..(36)
<223> OTHER INFORMATION: human adrenergic b2 receptor TM 6

<400> SEQUENCE: 35

Phe Cys Leu Lys Glu His Lys Ala Leu Lys Thr Leu Gly Ile Ile Met
 1               5                  10                  15

Gly Thr Phe Thr Leu Cys Trp Leu Pro Phe Phe Ile Val Asn Ile Val
                20                  25                  30

His Val Ile Gln
            35

<210> SEQ ID NO 36
<211> LENGTH: 36
<212> TYPE: PRT
<213> ORGANISM: Homo sapiens
<220> FEATURE:
<221> NAME/KEY: TRANSMEM
<222> LOCATION: (1)..(36)
<223> OTHER INFORMATION: human rhodopsin TM 6

<400> SEQUENCE: 36

Thr Gln Lys Ala Glu Lys Glu Val Thr Arg Met Val Ile Ile Met Val
 1               5                  10                  15

Ile Ala Phe Leu Ile Cys Trp Leu Pro Tyr Ala Gly Val Ala Phe Tyr
                20                  25                  30

Ile Phe Thr His
            35
```

-continued

```
<210> SEQ ID NO 37
<211> LENGTH: 20
<212> TYPE: PRT
<213> ORGANISM: Homo sapiens
<220> FEATURE:
<221> NAME/KEY: TRANSMEM
<222> LOCATION: (1)..(20)
<223> OTHER INFORMATION: human muscarinic acetylcholine m2 receptor TM 7

<400> SEQUENCE: 37

Gly Tyr Trp Leu Cys Tyr Ile Asn Ser Thr Ile Asn Pro Ala Cys Tyr
 1               5                  10                  15

Ala Leu Cys Asn
            20

<210> SEQ ID NO 38
<211> LENGTH: 20
<212> TYPE: PRT
<213> ORGANISM: Homo sapiens
<220> FEATURE:
<221> NAME/KEY: TRANSMEM
<222> LOCATION: (1)..(20)
<223> OTHER INFORMATION: human histamine H2 receptor TM 7

<400> SEQUENCE: 38

Val Leu Trp Leu Gly Tyr Ala Asn Ser Ala Leu Asn Pro Ile Leu Tyr
 1               5                  10                  15

Ala Ala Leu Asn
            20

<210> SEQ ID NO 39
<211> LENGTH: 20
<212> TYPE: PRT
<213> ORGANISM: Homo sapiens
<220> FEATURE:
<221> NAME/KEY: TRANSMEM
<222> LOCATION: (1)..(20)
<223> OTHER INFORMATION: human serotonin 5HT2A receptor TM 7

<400> SEQUENCE: 39

Phe Val Trp Ile Gly Tyr Leu Ser Ser Ala Val Asn Pro Leu Val Tyr
 1               5                  10                  15

Thr Leu Phe Asn
            20

<210> SEQ ID NO 40
<211> LENGTH: 20
<212> TYPE: PRT
<213> ORGANISM: Homo sapiens
<220> FEATURE:
<221> NAME/KEY: TRANSMEM
<222> LOCATION: (1)..(20)
<223> OTHER INFORMATION: human dopamine D2 receptor TM 7

<400> SEQUENCE: 40

Phe Thr Trp Leu Gly Tyr Val Asn Ser Ala Val Asn Pro Ile Ile Tyr
 1               5                  10                  15

Thr Thr Phe Asn
            20

<210> SEQ ID NO 41
<211> LENGTH: 20
<212> TYPE: PRT
<213> ORGANISM: Homo sapiens
<220> FEATURE:
```

```
<221> NAME/KEY: TRANSMEM
<222> LOCATION: (1)..(20)
<223> OTHER INFORMATION: human adrenergic b2 receptor TM 7

<400> SEQUENCE: 41

Ile Asn Trp Ile Gly Tyr Val Asn Ser Gly Phe Asn Pro Leu Ile Tyr
 1               5                  10                  15

Cys Arg Ser Pro
            20

<210> SEQ ID NO 42
<211> LENGTH: 20
<212> TYPE: PRT
<213> ORGANISM: Homo sapiens
<220> FEATURE:
<221> NAME/KEY: TRANSMEM
<222> LOCATION: (1)..(20)
<223> OTHER INFORMATION: human rhodopsin TM 6

<400> SEQUENCE: 42

Pro Ala Phe Phe Ala Lys Thr Ser Ala Val Tyr Asn Pro Val Ile Tyr
 1               5                  10                  15

Ile Met Met Asn
            20
```